(12) United States Patent
Arinaga et al.

(10) Patent No.: US 7,169,617 B2
(45) Date of Patent: Jan. 30, 2007

(54) DEVICE AND METHOD FOR QUANTITATIVELY DETERMINING AN ANALYTE, A METHOD FOR DETERMINING AN EFFECTIVE SIZE OF A MOLECULE, A METHOD FOR ATTACHING MOLECULES TO A SUBSTRATE, AND A DEVICE FOR DETECTING MOLECULES

(75) Inventors: Kenji Arinaga, Kawasaki (JP); Ulrich Rant, Garching (DE)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 11/036,367

(22) Filed: Jan. 18, 2005

(65) Prior Publication Data
US 2006/0040378 A1 Feb. 23, 2006

(30) Foreign Application Priority Data
Aug. 19, 2004 (JP) .............................. 2004-238980
Sep. 29, 2004 (JP) .............................. 2004-283245

(51) Int. Cl.
*G01N 33/543* (2006.01)
*G01N 33/551* (2006.01)
*G01N 33/553* (2006.01)
*G01N 15/06* (2006.01)
*G06F 19/00* (2006.01)

(52) U.S. Cl. ...................... 436/525; 436/518; 436/524; 702/27; 422/57; 422/68.1; 422/82.01

(58) Field of Classification Search ................ 435/5, 435/6, 7.1–7.9, 91.1–91.2, 288; 422/50, 422/68.1, 76, 186, 82.01–82.02, 82.05, 186.04; 204/180.1, 182.7–182.8; 427/569; 424/450; 210/634
See application file for complete search history.

(56) References Cited

U.S. PATENT DOCUMENTS 4,803,688 A * 2/1989 Lawandy ...................... 372/21
5,064,655 A * 11/1991 Uster et al. .................. 424/450

(Continued)

FOREIGN PATENT DOCUMENTS

JP 2001-235468 8/2001
WO WO 9418834 A1 * 9/1994

OTHER PUBLICATIONS

Suzuki et al., "Quantitative analysis of DNA orientation in stationary AC electric fields using fluorescence anistropy", 1998, IEEE Transactions on Industry Applications, vol. 34, pp. 75-83.*

(Continued)

*Primary Examiner*—Long V. Le
*Assistant Examiner*—Unsu Jung
(74) *Attorney, Agent, or Firm*—Armstrong, Kratz, Quintos, Hanson & Brooks, LLP

(57) ABSTRACT

A device for quantitatively determining an analyte is provided to conspicuously improve the performance of the quantitative determination. This device is equipped with a flow channel, an analyte detecting unit for capturing and detecting the analyte, and a quantitative measurement unit for quantitatively determining the analyte, wherein a signal generated when the analyte detecting unit has detected the analyte is divided into a plurality of parts in the direction of the flow in the flow channel at the quantitative measurement unit for processing. Also provided are technologies including one for controlling the density of molecules attached to the surface of a solid. In these technologies, when molecules are attached to a substrate, the density of attached molecules is controlled, by having an electrolyte also present in a solution containing the molecules to adjust the screening effect by the electrolyte, and by taking into consideration the effective size of a molecule.

6 Claims, 21 Drawing Sheets

ONE MOLECULE
ENLARGING

AREA OCCUPIED BY ONE MOLECULE IN CONSIDERATION OF THE DEBYE LENGTH: $2(r+ L_{Debye})^2 \sqrt{3}$
SURFACE DENSITY IN CONSIDERATION OF THE DEBYE LENGTH: $1/(2(r+ L_{Debye})^2 \sqrt{3})$
(ATTACHING DENSITY)

U.S. PATENT DOCUMENTS

| | | | |
|---|---|---|---|
| 5,106,468 A * | 4/1992 | Chimenti | 204/564 |
| 5,653,939 A * | 8/1997 | Hollis et al. | 422/50 |
| 5,952,095 A * | 9/1999 | Beall et al. | 428/332 |
| 6,616,987 B1 * | 9/2003 | Morfill et al. | 427/569 |
| 6,915,214 B2 * | 7/2005 | Dukhin et al. | 702/29 |
| 2002/0015792 A1 * | 2/2002 | Nagayama et al. | 427/299 |
| 2002/0070166 A1 * | 6/2002 | Backhouse | 210/634 |
| 2002/0126261 A1 * | 9/2002 | Nomura et al. | 353/31 |

OTHER PUBLICATIONS

Carbeck et al., "Measuring the size and charge of proteins using protein charge ladders, capillary electrophoresis, and electrokinetic models of colloids", 2001, J. Am. Chem. Soc., vol. 123, pp. 1252-1253.*

Hagerman et al., "Electrostatic contribution to the stiffness of DNA molecules of finite length", 1983, Biopolymers, vol. 22, pp. 811-814.*

A. Ulman; "Formation and Structure of Self-Assembled Monolayers;" *Chem. Rev.*; vol. 96; 1996; pp. 1533-1554.

S.O. Kelley, et al.; "Electrochemistry of Methylene Blue Bound to a DNA-Modified Electrode;" *Bioconjugate Chem.*; vol. 8; 1997; pp. 31-37.

A.W. Peterson, et al.; "The effect of surface probe density on DNA hybridization;" *Nucleic Acids Research*; vol. 29; No. 24; pp. 5163-5168.

T.M. Herne, et al.; "Characterization of DNA Probes Immobilized on Gold Surfaces;" *J. Am. Chem. Soc.*; vol. 119; 1997; pp. 8916-8920.

A.B. Steel, et al; "Electrochemical Quantitation of DNA Immobilized on Gold;" *Anal. Chem.*; vol. 70; 1998; pp. 4670-4677.

M.J. Heller; "DNA Microarray Technology: Devices, Systems and Applications;" *Annu. Rev. Biomed. Eng.*; vol. 4; 2002; pp. 129-153 and Fig. 1 (1 Sheet.).

* cited by examiner

FIG. 1-A
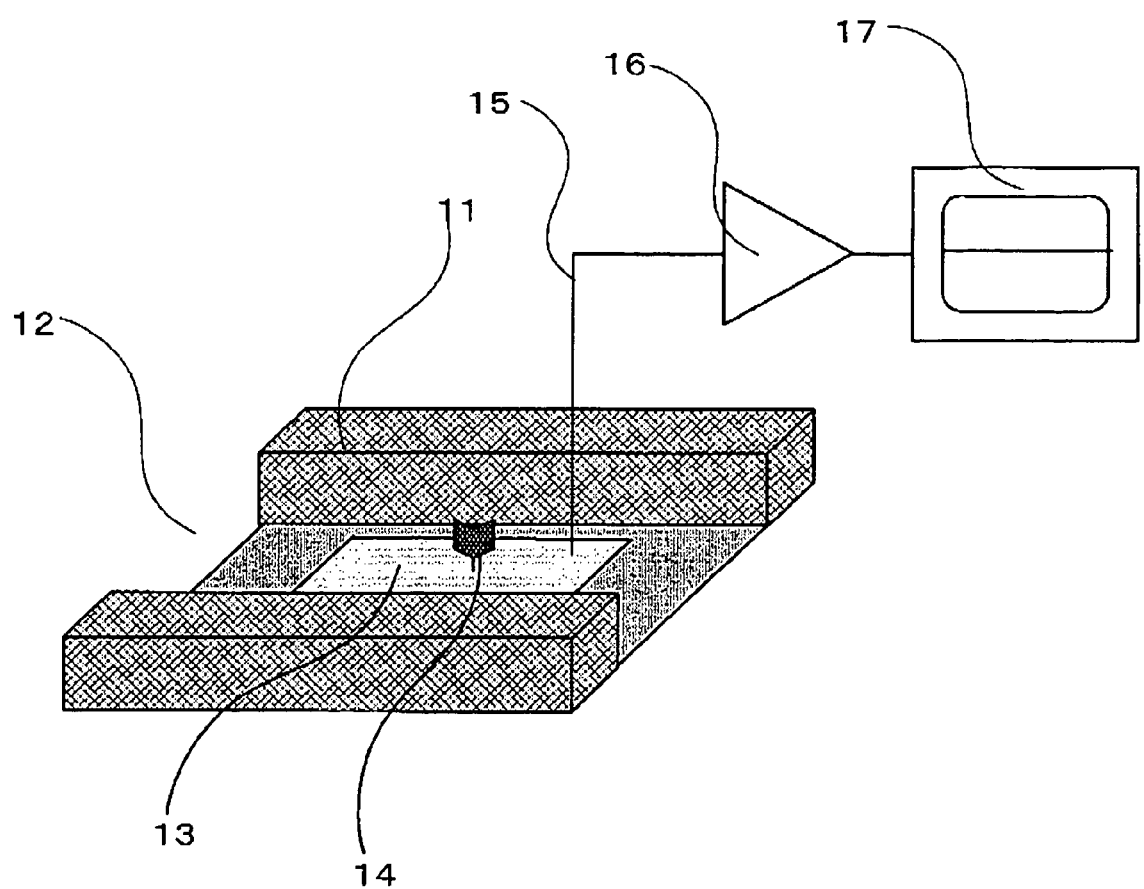

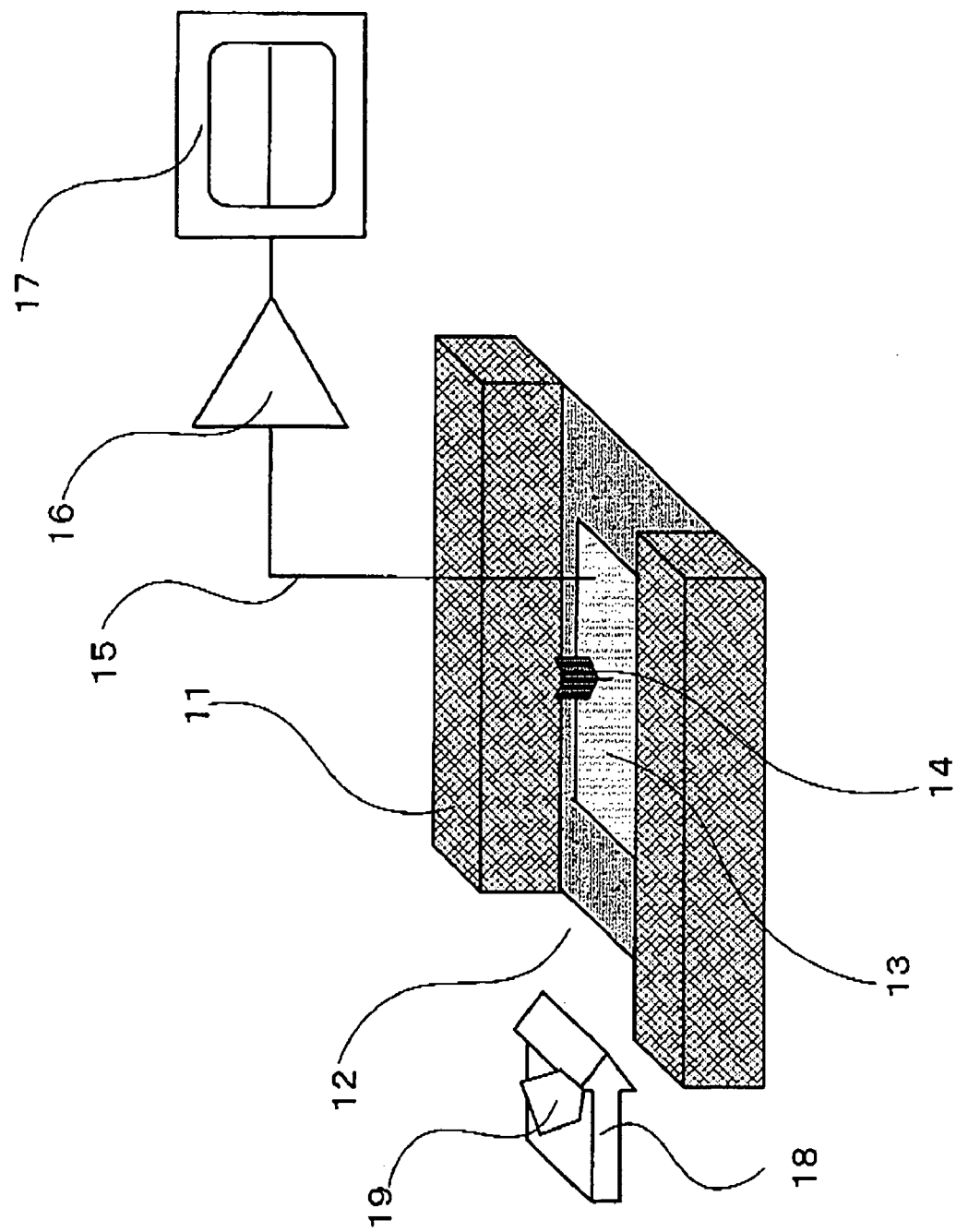
FIG. 1-B

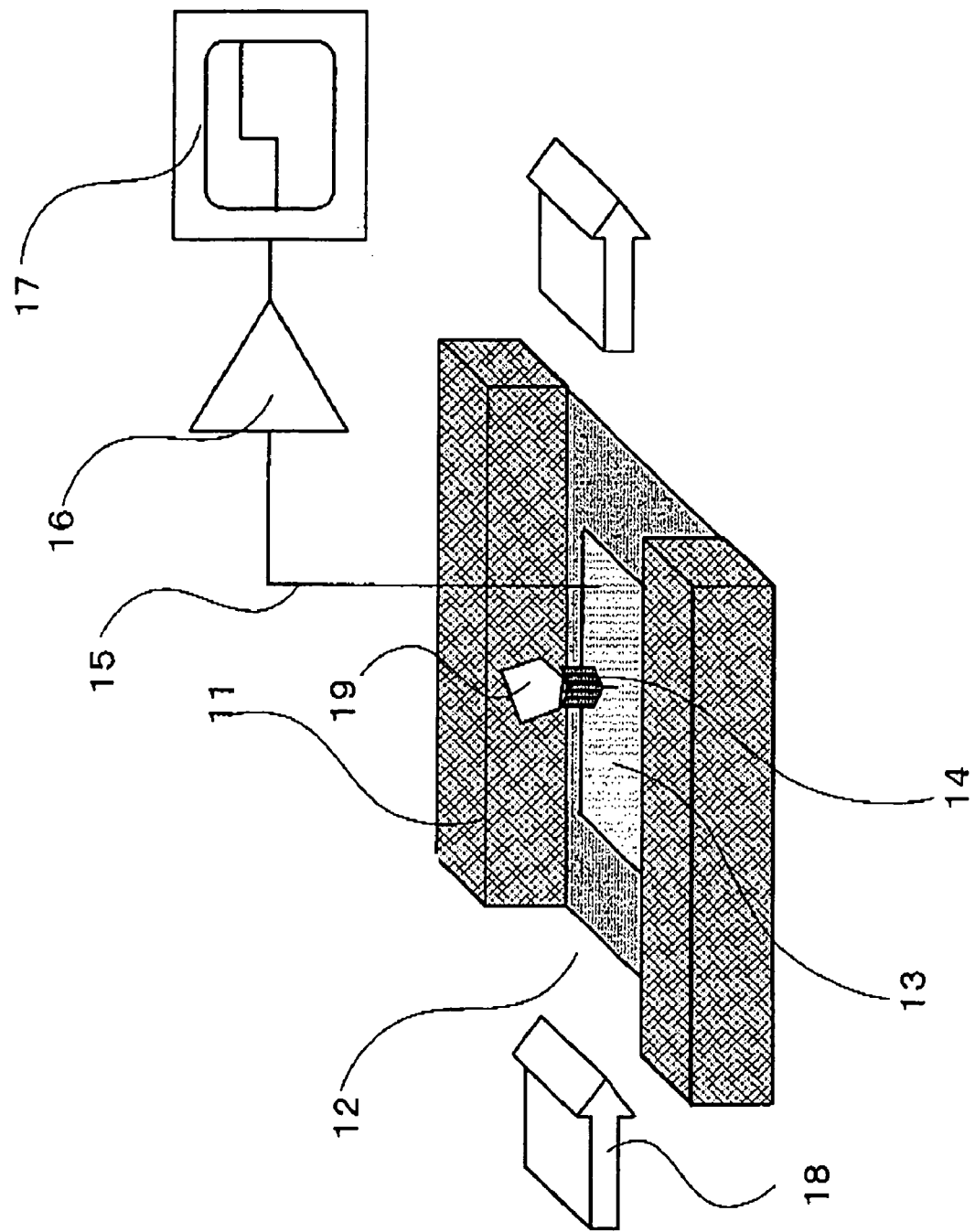

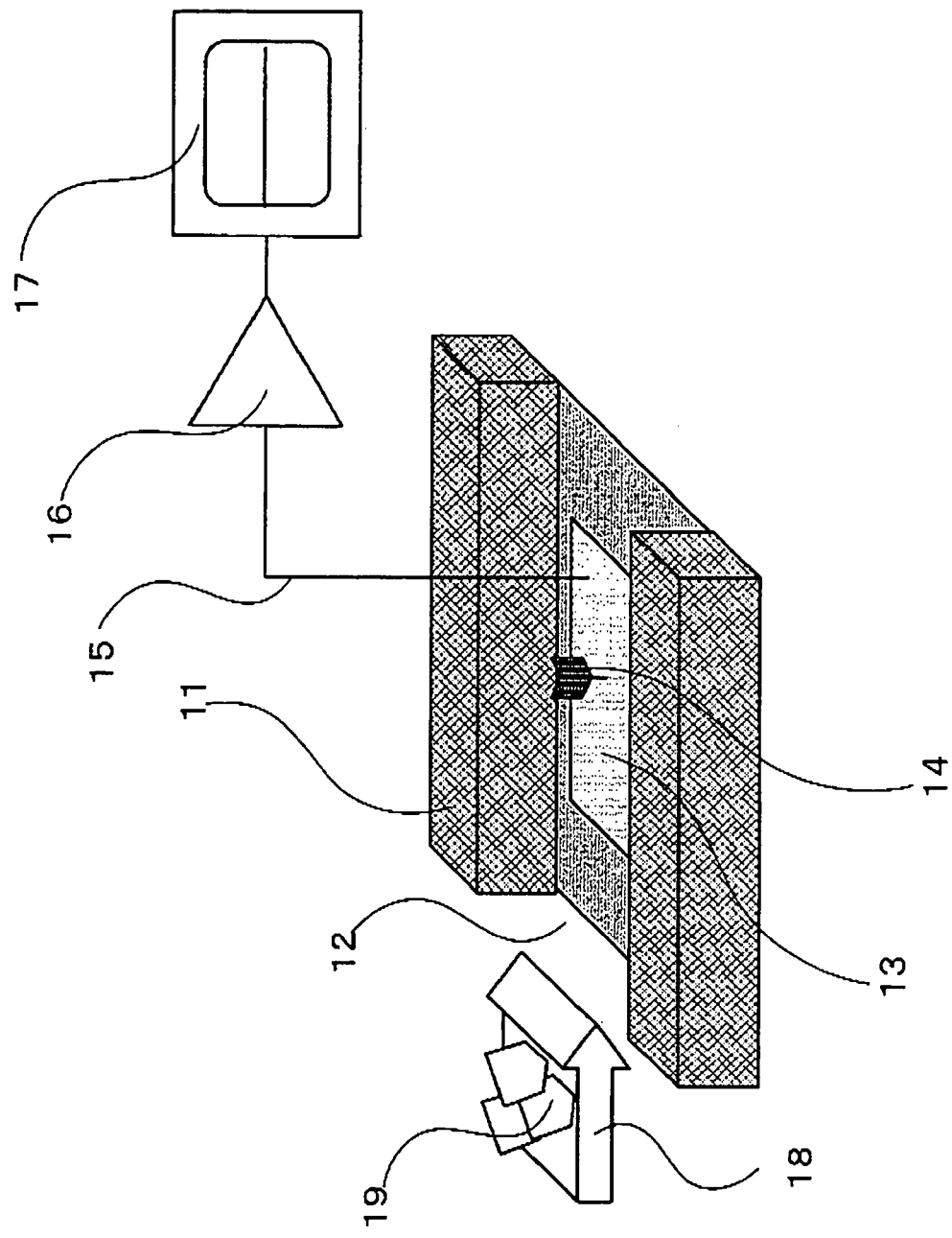
FIG. 2-A

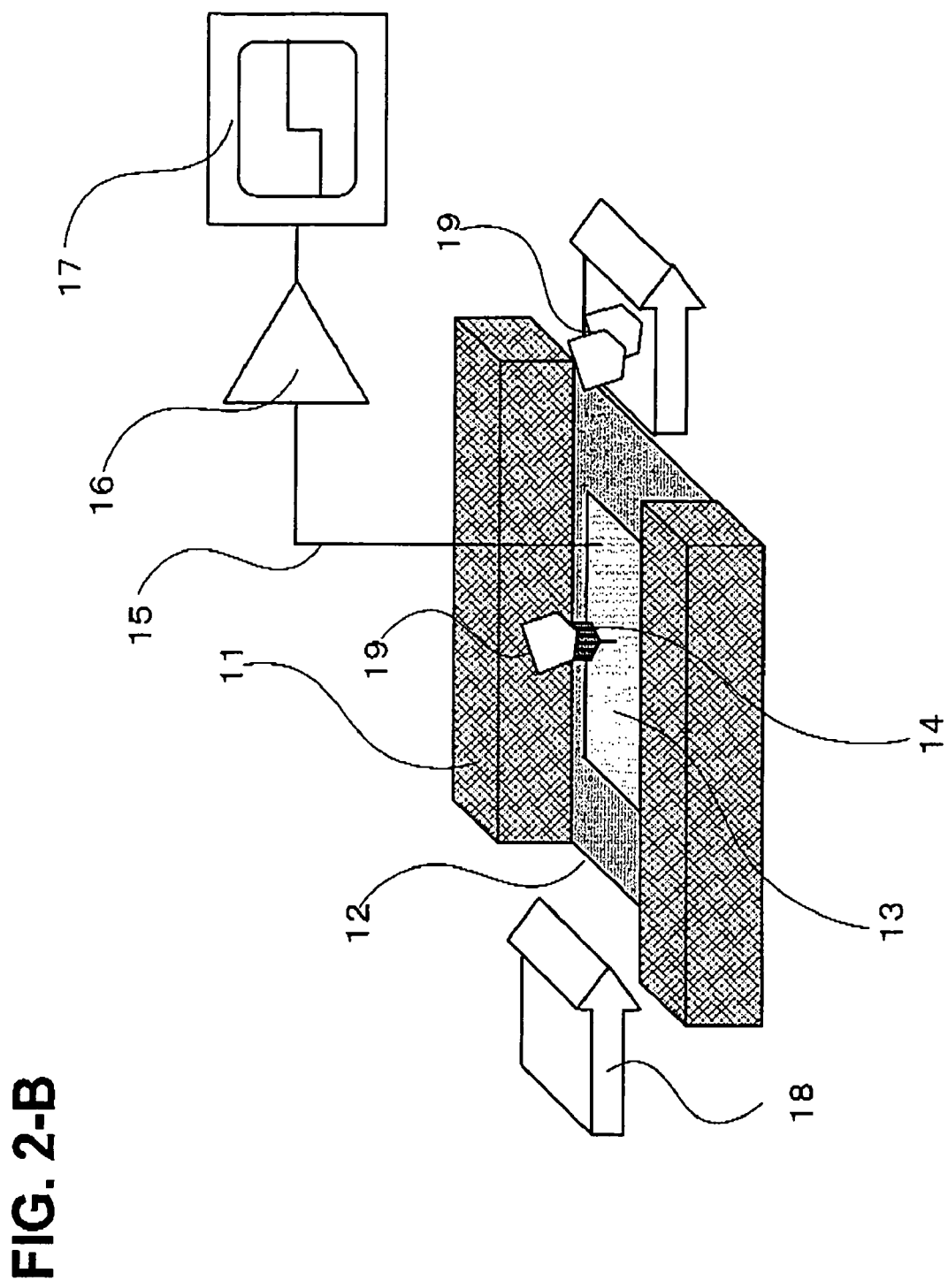
FIG. 2-B

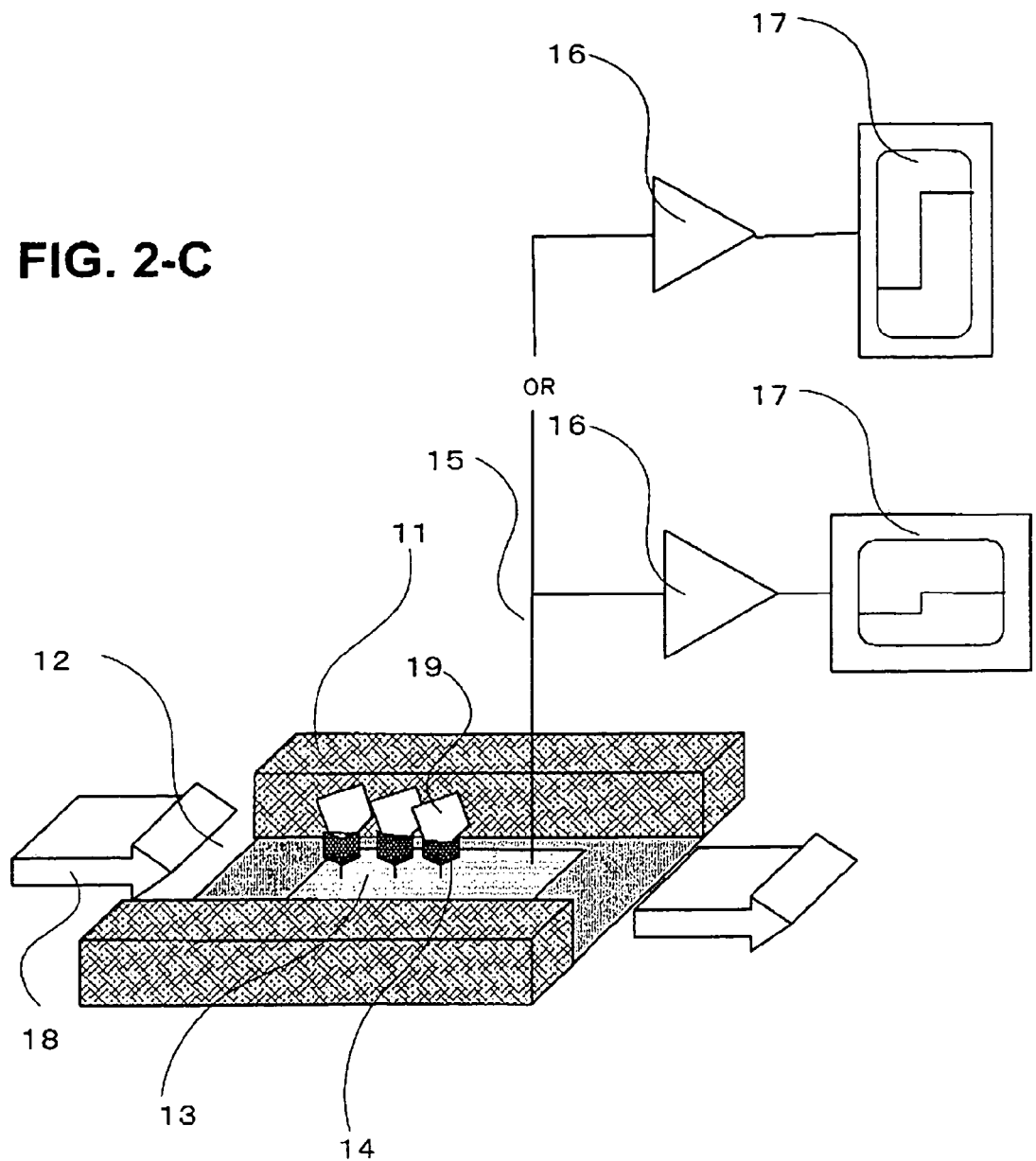
FIG. 2-C

FIG. 3-A
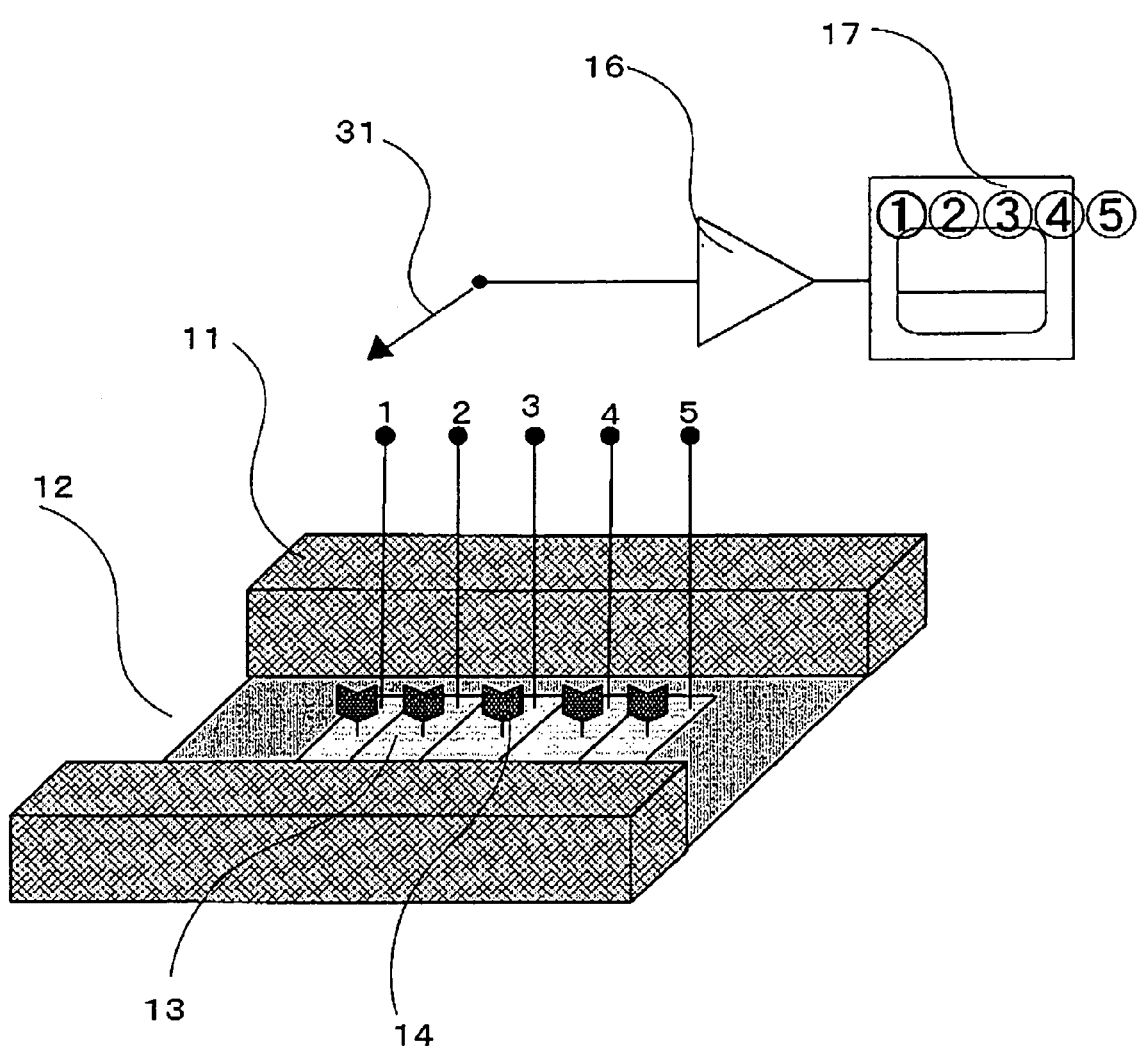

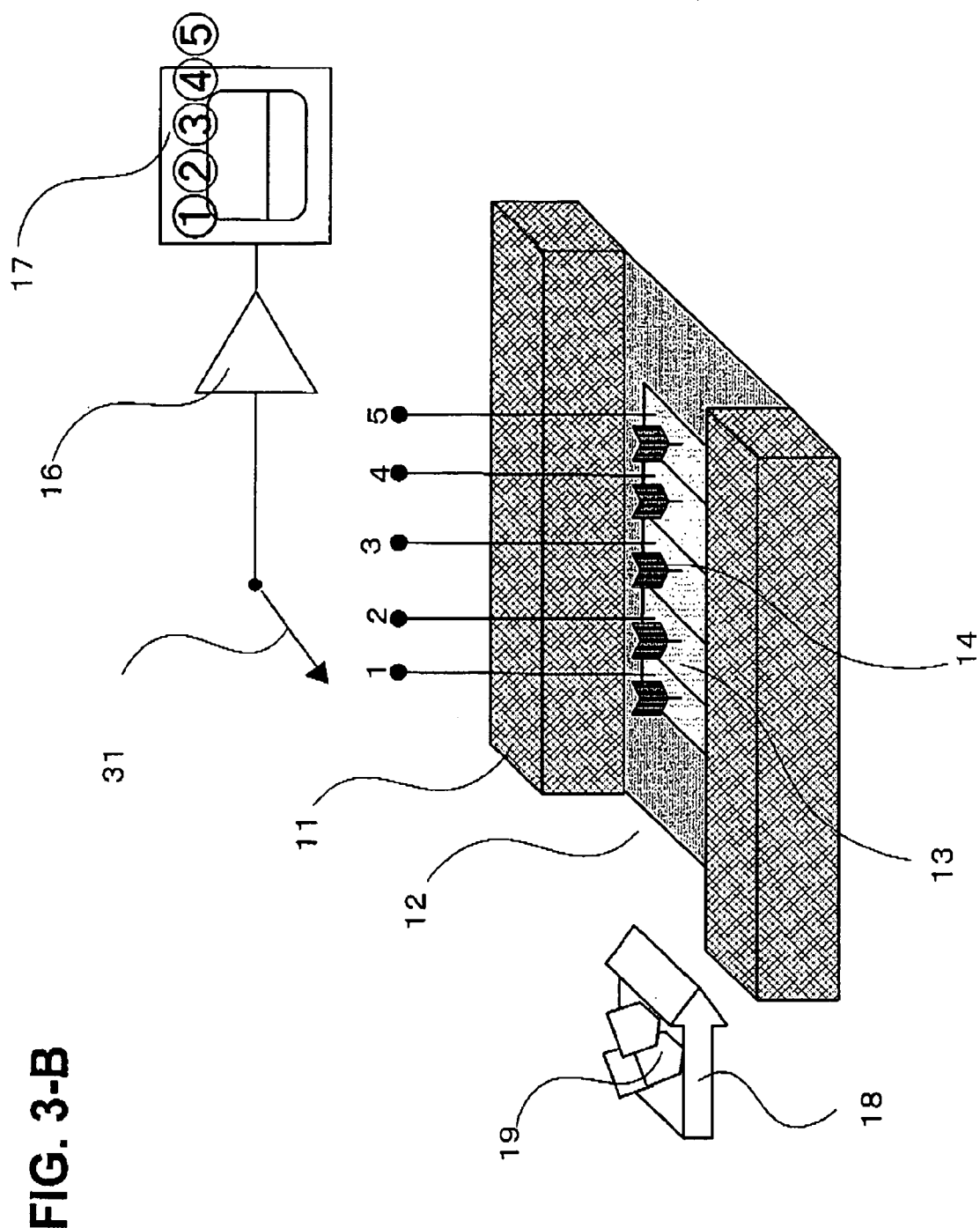
FIG. 3-B

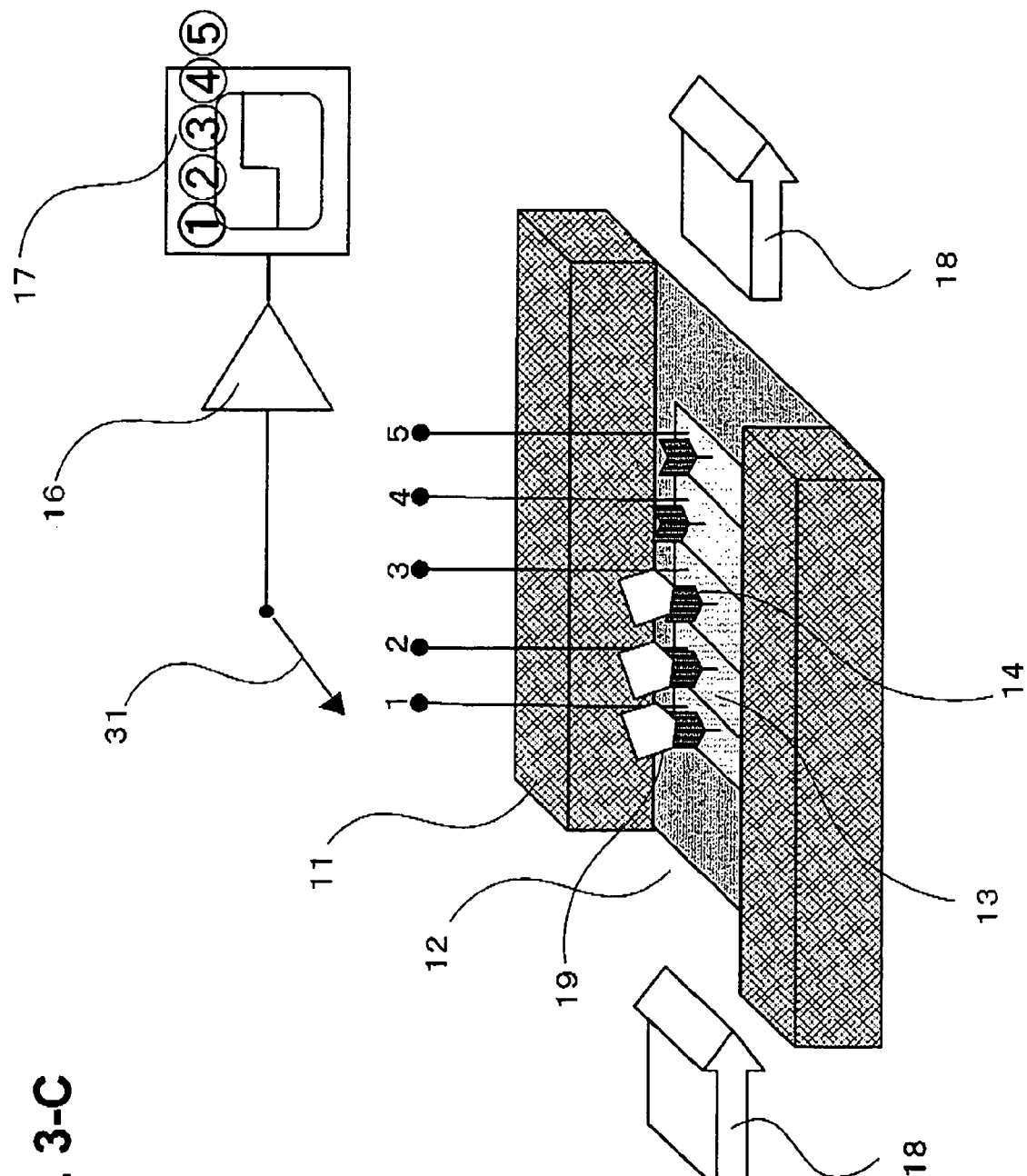
FIG. 3-C

FIG. 4-A
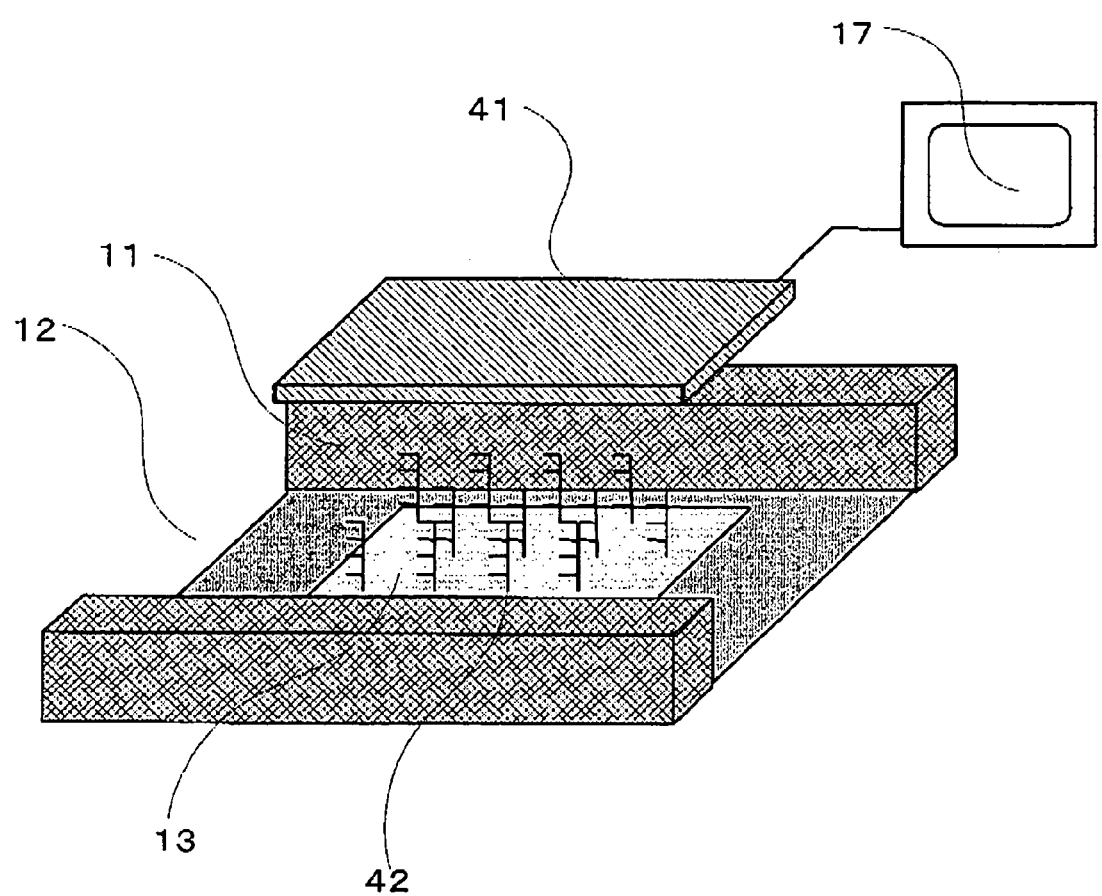

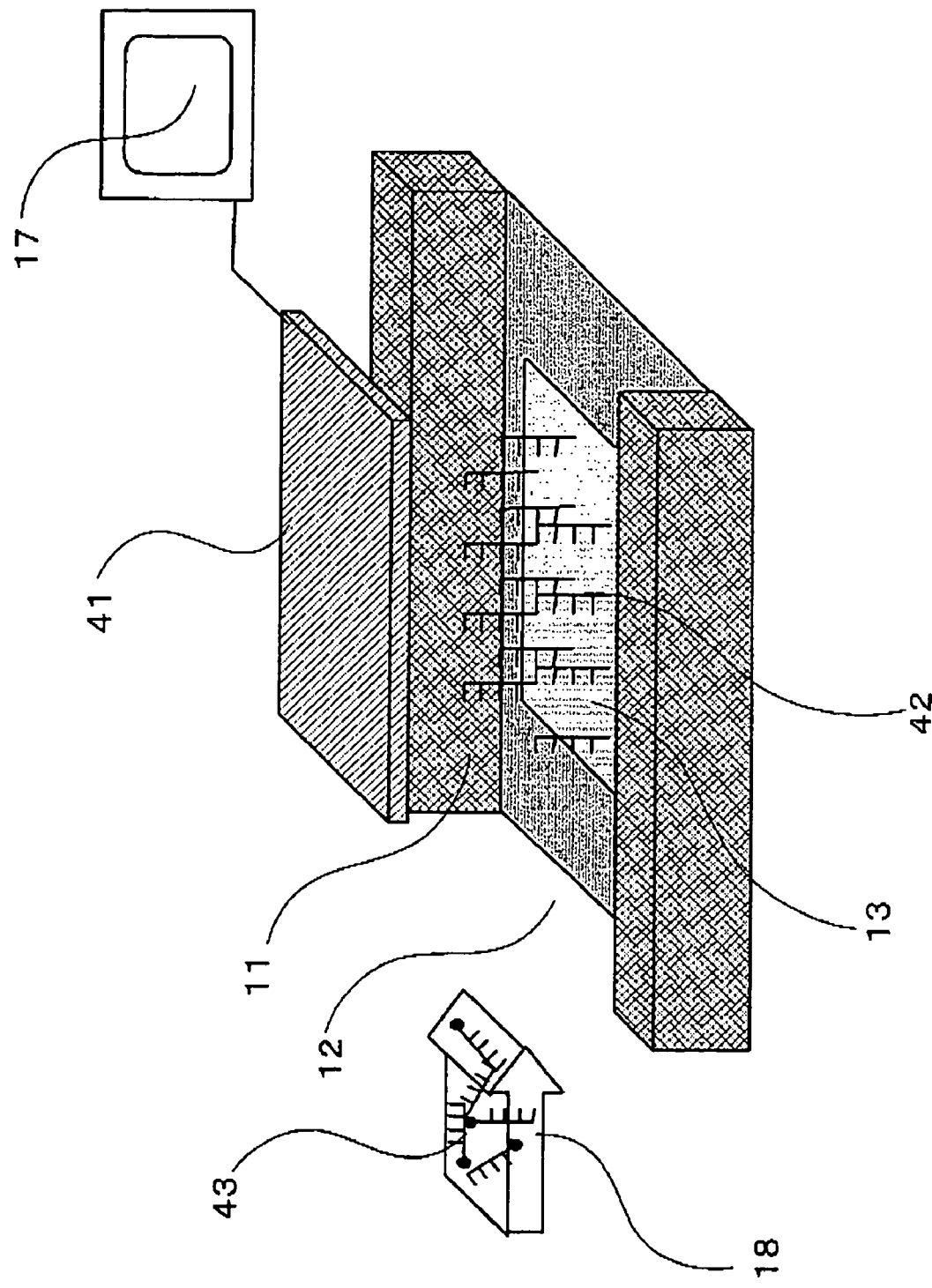

FIG. 4-C
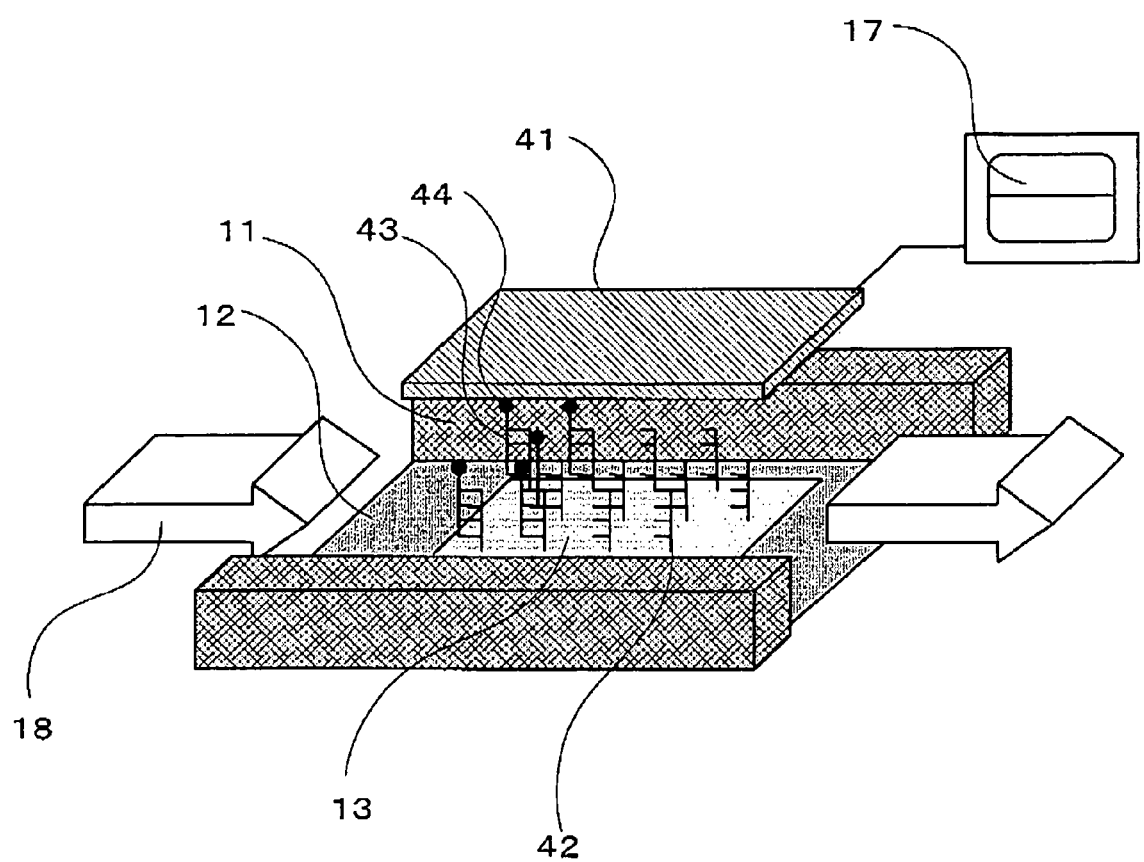

ONE MOLECULE

ENLARGING

AREA OCCUPIED BY ONE MOLECULE : $2r^2\sqrt{3}$
SURFACE DENSITY: $1/(2r^2\sqrt{3})$
(ATTACHING DENSITY)

DEVICE AND METHOD FOR QUANTITATIVELY DETERMINING AN ANALYTE, A METHOD FOR DETERMINING AN EFFECTIVE SIZE OF A MOLECULE, A METHOD FOR ATTACHING MOLECULES TO A SUBSTRATE, AND A DEVICE FOR DETECTING MOLECULES

CROSS-REFERENCE TO RELATED APPLICATIONS

This application is based upon and claims the benefit of priority from the prior Japanese Patent Application No. 2004-238980, filed on Aug. 19, 2004 and No. 2004-283245, filed on Sep. 29, 2004, the entire contents of which are incorporated herein by reference.

BACKGROUND OF THE INVENTION

1. Field of the Invention

The present invention relates to a method and device for quantitatively determining an analyte that is used for biochips, DNA chips, etc. as well as a method for attaching molecules to a substrate that is used for biochips, DNA chips, etc., and a device manufactured using the method.

2. Description of the Related Art

Recently nanotechnology has become a key word which has drawn much attention from many people, caused by various factors including a nanotechnology initiative proposed in United States in 2,000. Specifically, the nano-biotechnology field that is an integration of semiconductor microprocessing technologies (semiconductor nanotechnologies) and biotechnologies is expected as a new technical field that may bring about drastic solutions to the conventional problems, and many researchers are working energetically in this field.

Among these, the biochip technologies represented by DNA chips (or DNA microarrays) attract attention as an effective means for gene analysis. Biochips comprise substrates made of glasses, silicon, plastics, etc. on the surface of which numerous different test substances of biomacromolecules such as DNAs and proteins, are highly densely arrayed as spots. They can simplify examination of nucleic acids and proteins in the fields of clinical diagnosis and pharmacotherapy (see, for example, Japanese Unexamined Patent Application Publication No. 2001-235468 (paragraph numbers 0002–0009), and Annual Review of Biomedical Engineering, vol. 4, p. 129–153, 2002, and Nature Biotechnology, vol. 21, p. 1192–1199, 2003).

Devices, such as those chips, manufactured by integrating micromachining technologies and sensing technologies under technologies for detecting a tiny analyte, are generally called MEMSs or µTASs, which draw attention as devices for greatly improving the detection sensitivity and detection time compared with the prior art. The term MEMS is the abbreviation of Micro Electro Mechanical System, that is, a technology to prepare microscopic matters, based on semiconductor processing technologies, or microscopic, precision devices prepared, using the technologies. In general, it is a system wherein a plurality of functional units such as mechanical, optical and hydrodynamic units are integrated and miniaturized. The term µ-TAS is an abbreviation of Micro Total Analysis System, and is a chemical analysis system with micropumps, microvalves, sensors or the like, miniaturized, accumulated, and integrated.

The features of these devices are that it is possible to evaluate a very small amount of a sample containing an analyte, and that it is possible to perform a real-time evaluation by making a sample flow into an analyte detecting unit. There are many other advantages including one that it is possible to evaluate a plurality of analytes at the same time, by arranging analyte detecting units in parallel or in series.

Furthermore, regarding the technology that is a key for these nano-biotechnologies, there is an issue how biomolecules such as DNAs and proteins should be attached to a solid such as a semiconducting material and metal, in order to make the surface of the solid have a specific function. Attaching of molecules to the surface of a solid by physical adsorption represented by LB (Langmuir Brodgett) membranes have been long and widely known. However, the molecules formed only by physical adsorption are stripped off as time passes, or by repetitive use. Accordingly, attachment of molecules by chemical adsorption utilizing a chemical reaction between the surface of a solid and molecules has been generally used recently. Specifically, a method for attaching molecules by chemical adsorption wherein an SH (thiol) group is placed at an end of a molecule to utilize covalent bonding between S (sulfur) and a metal or semiconducting material, is proposed, and is widely used in various researches and developments (see, for example, Chemical Reviews, vol. 96, p. 1533–1554, 1996).

When molecules having an alkyl chain which has an SH end group is used as the molecules, a monomolecular film with a regular array of molecules can be formed on a solid, by means of van der Waals force of the alkyl chain. It is easy to form this membrane. That is, when the surface of a solid is immersed in a solution containing these molecules, a monomolecular film (self-assembled monolayer film) is spontaneously formed on the surface of the solid.

It is possible to form a monolayer film having a function on the surface, by attaching DNAs, proteins, or functional groups having other functions to a part of the alkyl chain (see, for example, Bioconjugate Chemistry, vol. 8, p. 31–37, 1997).

SUMMARY OF THE INVENTION

However, regarding the above-described device such as a MEMS and µTAS, though the presence or absence of an analyte can be detected when an extremely highly sensitive device is installed as the analyte detecting unit, there is a problem that the signal from the analyte detecting unit may be saturated by a small amount of analyte, and accordingly it is difficult to quantitatively determine the analyte, if the device characteristics are not sufficiently linear to the amount of analyte (in other words, if the dynamic range is low for the amount of analyte).

Particularly in detecting biomolecules with a biochip or the like, molecules such as antibody molecules that are specifically adsorbed to the biomolecules, are often used as the analyte detecting units. In such a case, an analyte detecting unit and an analyte are often bound in a 1:1 ratio, whereby a small number of analytes will saturate the analyte detecting units if the number of analyte detecting units is small, making it impossible to perform quantitative determination in a wide range. On the other hand, if the number of analyte detecting units is increased to make it possible to perform quantitative determination in a wide range, it will cause degradation of the detection sensitivity and increase of background noises.

The first aspect of the present invention is directed to solving the above-described problem, and providing a new technology with which it is possible to quantitatively determine an analyte in a wide range without lowering the detection sensitivity, even when an analyte detecting unit is bound to an analyte in a 1:1 ratio, as is observed in the case of a biochip.

According to one embodiment of the first aspect of the present invention, provided is a device for quantitatively determining an analyte equipped with a flow channel, an analyte detecting unit for capturing and detecting the analyte, and a quantitative measurement unit for quantitatively determining the analyte, wherein a signal generated when the analyte detecting unit has detected the analyte is divided into a plurality of parts in the direction of the flow in the flow channel at the quantitative measurement unit for processing.

Using the device for quantitatively determining an analyte according to this embodiment of the present invention makes it possible to quantitatively determine an analyte in a wide range without lowering the detection sensitivity, with the result that the performance in quantitative determination of an analyte is conspicuously improved.

In this embodiment, preferable are that the analyte detecting unit has an analyte capturing unit for capturing the analyte; that a plurality of analyte detecting units are disposed in the direction of the flow in the flow channel; that the length of the analyte detecting unit in the direction of the flow in the flow channel is not less than twice the width of the flow channel; that a plurality of analyte detecting units are disposed in the direction along the width of the flow channel; that the quantitative measurement unit quantitatively determines the analyte, using an optical signal; that the quantitative measurement unit quantitatively determines the analyte, using an electric signal; that the thickness of the flow channel at the analyte detecting unit is not more than 100 times the effective height of a captured analyte; that the thickness of the flow channel at the analyte detecting unit is made larger as the flow goes downstream; that the analyte detecting unit is an electrode to which an electric potential can be applied for electrically attracting charged analytes to the electrode; particularly that the electric potential for electrically attracting charged analytes to the electrode can be changed according to the location of the electrode in the direction of the flow; that a micropump, electrophoretic flow or electroosmotic flow is utilized to make a solution containing the analyte flow in the flow channel; that a plurality of analyte capturing units for specifically capturing different analytes, are disposed on the analyte detecting unit; that the analyte is a DNA, and the analyte capturing unit has a function to be specifically bound to a DNA; and that the analyte is a protein, and the analyte capturing unit has a function to be specifically bound to a protein.

According to another embodiment of the first aspect of the present invention, provided is a method for quantitatively determining an analyte comprising: using a flow channel, an analyte detecting unit for capturing and detecting the analyte, and a quantitative measurement unit for quantitatively determining the analyte; and dividing a signal generated when the analyte detecting unit has detected the analyte, into a plurality of parts in the direction of the flow in the flow channel at the quantitative measurement unit for processing.

Using the method for quantitatively determining an analyte according to this embodiment of the present invention makes it possible to quantitatively determine an analyte in a wide range without lowering the detection sensitivity, with the result that the performance in quantitative determination of an analyte is conspicuously improved.

In this embodiment, preferable are that the analyte detecting unit has an analyte capturing unit for capturing the analyte; that a plurality of analyte detecting units are disposed in the direction of the flow in the flow channel; that the number of analytes captured by the analyte detecting unit in the direction of the flow in the flow channel is optimized; more specifically that the optimization is performed by changing at least one factor selected from the group consisting of the supplying velocity of the analyte, the length of the analyte detecting unit in the direction of the flow in the flow channel, the number of the analyte detecting units in the direction along the width of the flow channel, and the thickness of the flow channel; that the quantitative measurement unit quantitatively determines the analyte, using an optical signal; that the quantitative measurement unit quantitatively determines the analyte, using an electric signal; that the analyte detecting unit is an electrode, and an electric potential for electrically attracting charged analytes to the electrode, is applied to the electrode; particularly that the electric potential for electrically attracting charged analytes to the electrode is changed according to the location of the electrode in the direction of the flow; that a plurality of analyte capturing units for specifically capturing different analytes, are disposed on the analyte detecting unit; that the analyte is a DNA, and the analyte capturing unit has a function to be specifically bound to a DNA; and that the analyte is a protein, and the analyte capturing unit has a function to be specifically bound to a protein.

According to other embodiments of the first aspect of the present invention, provided are a MEMS and µTAS equipped with the above-described device for quantitatively determining an analyte.

By the above-described first aspect of the present invention, it is possible to quantitatively determine an analyte in a wide range without lowering the detection sensitivity, with the result that the performance in quantitative determination of an analyte is conspicuously improved.

Regarding the attachment of biomolecules, when the surface of a solid is modified simply with molecules comprising an alkyl chain having functional groups that have various functions, there is a problem that it is difficult to control the density of the molecules comprising the alkyl chain attached to the surface (the density of molecules attached to the surface of a solid such as a substrate is referred to as the "attaching density" in the present invention).

In addition, even though it is known that such chemical adsorption of molecules is dependent on diffusion, and there is an example reporting a change in the attaching density of molecules observed with time, a state of a relatively low attaching density is attained in a short time, and therefor, it is difficult to realize, with a high reproducibility, a low attaching density with wide spacing between adjacent molecules for which the influence of interactions between molecules can be ignored, by controlling the time for preparation (see Nucleic Acids Research, vol. 29, p. 5163–5168, 2001, for example).

Furthermore, biomolecules such as DNAs and proteins are relatively large compared with usual molecules having an alkyl chain. Accordingly, if a self-assembled monolayer film that is compact (that is, having a high density of biomolecules) is simply prepared, steric hindrance between biomolecules becomes large, posing a problem of hindering free motion of the biomolecules. On such a surface, it is not possible to sufficiently acquire signals related to reactions between the biomolecules, their thermal motions (signals related to fluctuating motion and bending/stretching motions, for example), etc.

On the other hand, in the field of biosensors which utilize reactions between such molecules and/or motions of molecules for a sensing technology, it is very important to control the attaching density and/or to realize a low attaching density with a high reproducibility. Accordingly, there is a strong need for a technology to control the density of molecules attached to the surface of a solid.

A DNA has a negative charge in an aqueous solution on the phosphoric acid group on its back bone. Accordingly, DNA molecules electrostatically repel each other in an aqueous solution. In an aqueous solution containing an electrolyte, it is also known that ions having a positive charge surround a DNA molecule, indicating an action of compensating the electric charge of the DNA molecule (called the screening effect, or Debye effect).

This screening effect is dependent on the concentration of an electrolyte. That is, it is possible to control the closest distance between DNA molecules, by controlling the concentration of an electrolyte, thus providing a possibility of controlling the eventual attaching density of molecules having an electric charge such as DNA molecules.

However, though there are some reports confirming such an effect, they are only qualitative studies, and cannot predict the attaching density (see Journal of American Chemical Society, vol. 119, p. 8916–8920, 1997, for example).

Furthermore, much is unknown what structure molecules in the shape of a strand such as DNS molecules have in an aqueous solution, which makes it all the more difficult to handle such molecules.

The second aspect of the present invention is directed to solving the above-described problems, and to provide a technology to control the density of molecules attached to the surface of a solid.

It is also directed to providing technologies that can clarify the structure and behavior of molecules attached to the surface of a solid in a solution, and realize a device using molecules attached to the surface of a solid, with high reliability and high sensitivity.

Other objects and advantages of the present invention will be clarified in the following explanation.

According to one embodiment of the second aspect of the present invention, provided is a method for determining an effective size of a molecule having an electric charge, wherein the effective size of a molecule having an electric charge in a solution containing an electrolyte and the molecule having an electric charge is estimated, using the screening effect by the electrolyte.

By this embodiment of the present invention, it is possible to know the effective size of a molecule having an electric charge for controlling the attaching density of molecules attached to the surface of a solid.

According to another embodiment of the second aspect of the present invention, provided is a method for attaching molecules having an electric charge to a substrate, wherein the attaching density of molecules is controlled, by having an electrolyte present in a solution containing the molecules to adjust the screening effect by the electrolyte, and by taking into consideration the effective size of a molecule in a solution, when the molecules having an electric charge are attached to the substrate.

By this embodiment of the present invention, it is possible to realize a required attaching density.

It is preferable that the effective size of a molecule having an electric charge in a solution containing an electrolyte and the molecule having an electric charge is estimated from the screening effect by the electrolyte as explained above, and the thus obtained effective size is used as the above-described effective size.

In addition, while any electrolyte may be used in any of the above-described embodiments, preferable are that an electrolyte composed of a monovalent cation and a monovalent anion is used as the electrolyte; and that the electrolyte comprising a monovalent cation and a monovalent anion is NaCl, KCl or a mixture thereof.

According to still another embodiment of the second aspect of the present invention, provided is a device for attaching molecules having an electric charge to a substrate, wherein the density of molecules attached to the substrate can be controlled, using the method for attaching molecules to a substrate according to the above-described method. By this embodiment of the present invention, it is possible to obtain a substrate having a desired attaching density.

According to still another embodiment of the second aspect of the present invention, provided is a device for detecting molecules, wherein the above-described method for attaching molecules to a substrate is used, and a substrate of which the attaching density is controlled so that the distance between adjacent molecules attached to the substrate is not less than twice or less than twice the effective length of a molecule, is used as a molecule detecting unit.

By this embodiment of the present invention, it is possible to clarify the structures and behaviors of molecules attached to the surface of a solid in a solution, and realize a device with high reliability and high sensitivity.

It is preferable that the substrate is made of an electro-conductive material, a semiconducting material, or an insulating material, and particularly made of gold or platinum.

Also preferable in each embodiment of the present invention are that the molecule having an electric charge comprises a material selected from the group consisting of proteins, DNAs, RNAs, antibodies, natural or artificial single-stranded nucleotides, natural or artificial double-stranded nucleotides, aptamers, products obtained by limited decomposition of antibodies with a protease, organic compounds having affinity to proteins, biomacromolecules having affinity to proteins, complex materials thereof, ionic polymers charged positively or negatively, and arbitrary combinations thereof; that the molecule having an electric charge comprises a thiol group; and that the molecule having an electric charge comprises a fluorescent pigment.

By this embodiment of the present invention, it is possible to control the attaching density of molecules attached to the surface of a solid, whereby it is possible to clarify the structure and behavior of the molecules attached to the surface of a solid in a solution. It is also possible to realize a device using the molecules attached to the surface of a solid with high reliability and high sensitivity.

Each of the above-described two aspects of the present invention can be applied to the other aspect. For example, the device according to the first aspect can be used for determining an effective size of a molecule having an electric charge, and the method for attaching molecules having an electric charge to a substrate according to the second aspect can be used for a detecting unit in the device according to the first aspect.

BRIEF DESCRIPTION OF THE DRAWINGS

FIG. 1-A is a schematic view explaining how an analyte is detected by a conventional device for quantitatively determining an analyte;

FIG. 1-B is a schematic view explaining how an analyte is detected by a conventional device for quantitatively determining an analyte;

FIG. 1-C is a schematic view explaining how an analyte is detected by a conventional device for quantitatively determining an analyte;

FIG. 2-A is a schematic view explaining how an analyte is detected by a conventional device for quantitatively determining an analyte;

FIG. 2-B is a schematic view explaining how an analyte is detected by a conventional device for quantitatively determining an analyte;

FIG. 2-C is a schematic view explaining how an analyte is detected by a conventional device for quantitatively determining an analyte;

FIG. 3-A is a schematic view explaining how an analyte is detected by a device for quantitatively determining an analyte according to the present invention;

FIG. 3-B is a schematic view explaining how an analyte is detected by a device for quantitatively determining an analyte according to the present invention;

FIG. 3-C is a schematic view explaining how an analyte is detected by a device for quantitatively determining an analyte according to the present invention;

FIG. 4-A is a schematic view explaining how an analyte is detected by a device for quantitatively determining an analyte according to the present invention;

FIG. 4-B is a schematic view explaining how an analyte is detected by a device for quantitatively determining an analyte according to the present invention;

FIG. 4-C is a schematic view explaining how an analyte is detected by a device for quantitatively determining an analyte according to the present invention;

DESCRIPTION OF THE PREFERRED EMBODIMENTS

Figure 5:
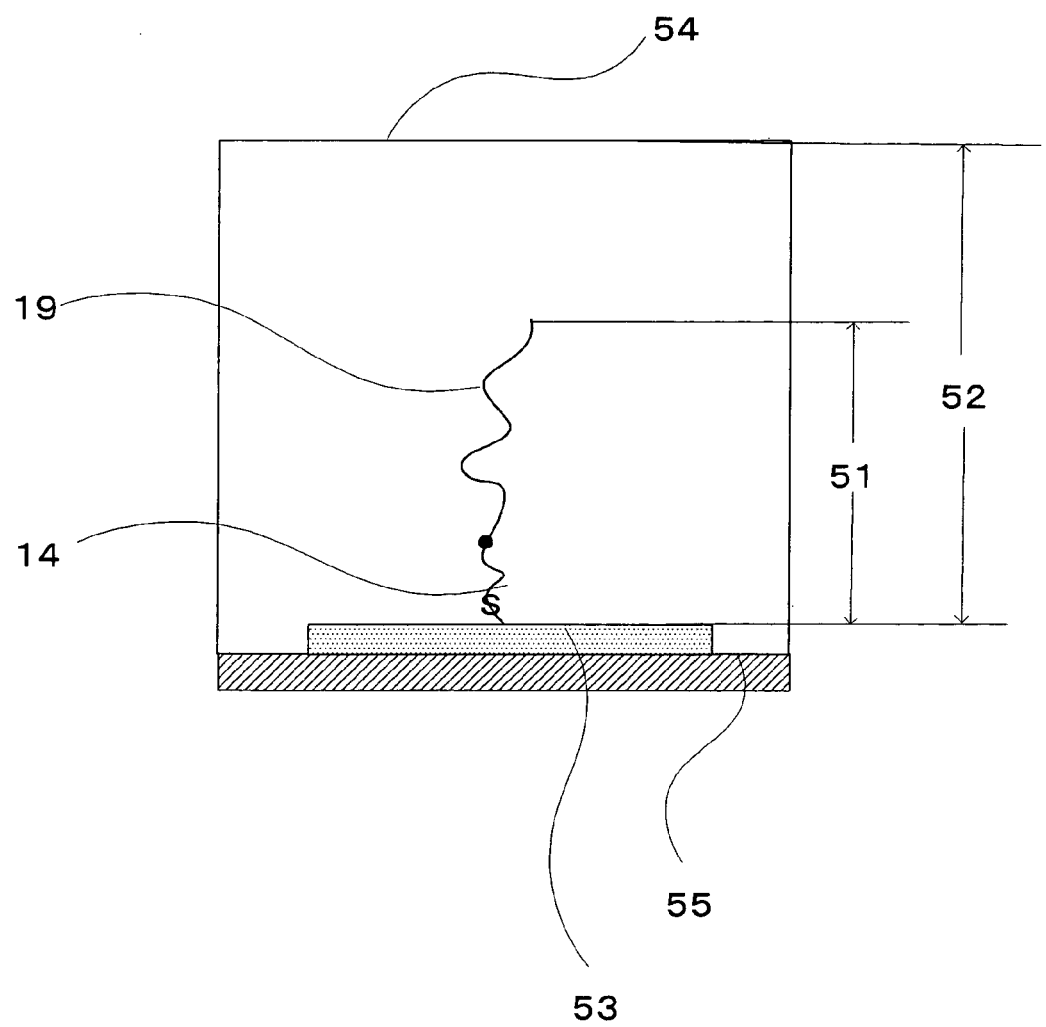
FIG. 5 is a schematic view explaining the thickness of a flow channel and the height of an analyte.

Embodiments according to the present invention will now be described using drawings, examples, etc. These drawings, examples, etc., and descriptions are for demonstrating the present invention, and do not limit the scope of the invention. Needless to say, other embodiments can be included in the scope of the present invention as long as they conform to the essential character according to the present invention. The same reference numeral indicates the same element in the drawings.

The device for quantitatively determining an analyte according to the first aspect of the present invention, is equipped with a flow channel, an analyte detecting unit (also referred to as a "detecting unit" hereinafter) for capturing and detecting the analyte, and a quantitative measurement unit for quantitatively determining an analyte, wherein a signal generated when the detecting unit has detected an analyte is divided into a plurality of parts in the direction of the flow in the flow channel at the quantitative measurement unit for processing. By this, it is possible to quantitatively determine an analyte with a high sensitivity and a high dynamic range.

Any signal may be used as a signal that is processed at the quantitative measurement unit for quantitatively determining the analyte. However, an electric signal or optical signal is highly reliable, and accordingly preferable.

Any method may be used as a method for the detecting unit to capture the analyte. A method in which the detecting unit has an analyte capturing unit for capturing an analyte (also simply referred to as "capturing unit", hereinafter) is the easiest method, and is preferable. Although the detecting unit and the capturing unit are generally separately explained in the following explanation, it is permissible to include the capturing unit into the detecting unit and call the whole of them as a detecting unit, as long as it does not contradict the gist of the present invention.

Any method may be used as a method in which the quantitative measurement unit can divide the signal generated when the detecting unit has detected the analyte, into plural parts for processing in the direction of the flow in the flow channel. When the quantitative measurement unit quantitatively determines an analyte using an optical signal, an optical signal such as fluorescence over the detecting unit may be scanned, or an optical signal over the detecting unit may be received as a whole, and the image is divided into plural parts for analysis.

In the case of an optical signal, it is easy to observe it by dividing it into plural parts, without dividing the source of the signal into plural parts beforehand. However, when the quantitative measurement unit quantitatively determines an analyte by an electric signal, it is necessary to install a plurality of separate detecting units in the direction of the flow in the flow channel so as to take out a plurality of electric signals.

The term "in the direction of the flow in the flow channel" refers to "in the direction along which a medium containing an analyte flows in the flow channel", and the act of "dividing into plural parts in the direction of the flow in the flow channel for processing" may be, for example, realized by scanning an optical signal in the direction of the flow in the flow channel, or by installing a plurality of detecting units in the direction of the flow in the flow channel, and taking out electric signals from each of the detecting units. It is to be noted that the "direction of the flow in the flow channel" in this case is not necessarily a straight line direction. For example, it is not necessary to install a plurality of detecting units on a straight line. Such signals may be combined with scanning of an optical signal in the direction along the width of the flow channel, and when there are a plurality of detecting units in the direction along the width of the flow channel, electric signals from these detecting units may be used together with the above-described signals.

The following is an explanation of a case in which a capturing unit is installed on a detecting unit, and a quantitative measurement unit quantitatively determines an analyte by an electric signal, in reference to FIGS. 1–3.

FIGS. 1–3 are schematic views of devices for quantitatively determining an analyte for explaining the principles of conventional examples and the first aspect of the present invention. In FIGS. 1–3, a device for quantitatively determining an analyte 11 for uses such as MEMSs and μTASs has a detecting unit 13 equipped with a capturing unit 14 that specifically binds to an analyte in a 1:1 ratio in a flow channel 12, and generates an electric signal when bound.

A conventional device for quantitatively determining an analyte will be explained, using FIGS. 1-A to 1-C, and FIGS. 2-A to 2-C. The device for quantitatively determining an analyte 11 is equipped with one capturing unit on the detecting unit as shown in FIG. 1-A, a solution for inspection (inspection solution) 18 comprising an analyte 19 flows in the flow channel as shown in FIG. 1-B, and when it passes through an inspection unit 13, the analyte 19 is specifically bound to the capturing unit 14, generating an electric signal, as shown in FIG. 1-C. This signal is taken out through a signal receiving electrode 15, necessary processing (amplification, conversion, etc.) is performed at a signal processing circuit 16, and ascertained as a changing signal on a monitor 17.

When one capturing unit 14 is used for the detecting unit 13, as is the case for the conventional examples, only one of the analytes is bound to the capturing unit, generating a signal as shown in FIG. 2-B, when a solution 18 containing two or more analytes 19 flows into the flow channel 12 as shown in FIG. 2-A. Accordingly, the remaining analytes flow out of the flow channel, without being bound to the capturing unit, with the result that it is impossible to quantitatively determine the analytes precisely.

Furthermore, when three capturing units are installed on the detecting unit to increase the capacity of quantitative determination three times, for example, as shown in FIG. 2-C, it is necessary to raise the dynamic range to correspond to the electric signal that is three times as large (a monitor 17 shown at the upper side of the figure), or decrease the sensitivity to one third (a monitor 17 shown at the lower side of the figure).

To compare, the "detecting unit" is divided into plural parts in the direction of the flow in the flow channel for the processing, according to the present invention. For example, FIG. 3-A shows five detecting units 13 each having one capturing unit 14 (designated by numerals 1–5) that are electrically separated from each other, are installed in series in the direction of the flow in the flow channel.

In addition, a switching electrode 31 is installed to monitor signals from the electrodes in a alternate manner. In this way, when analytes flown in the flow channel are bound to the capturing units sequentially from the upstream side to the downstream side as shown in FIG. 3-B, signals are generated sequentially from the upper detecting unit to the lower detecting unit according to the amount (that is number) of the analytes.

In such a case, the signals from the detecting units represented by circled numbers 1–5 in the figure obtained by the sequential switching as shown in FIG. 3-C are subjected to necessary processing (amplification, conversion, etc.) by the signal processing circuit 16. When the amount (or number) of the analytes in the solution is three, signals from the uppermost detecting unit to the third one are detected through continuous monitoring by the monitor 17, thus making it possible to quantitatively determine the amount of analytes by the locations of the detecting units through which signals are observed. These switching electrode 31, signal processing circuit 16 and monitor 17 constitute the quantitative measurement unit according to the present invention.

Utilizing the present invention, it is possible to increase the capacity for quantitatively determining an analyte by combining a conventional signal processing circuit with a simple switch, for example, and improve the dynamic range of the detecting device without lowering the sensitivity.

The above explanation is made to a case when one capturing unit is installed on a detecting unit. Similar effect can also be provided when a plurality of capturing units are installed on a detecting unit, taking into consideration a case when a large number of analytes are present. Generally speaking, as it is not easy to install only one capturing unit on a detecting unit, it is often practical to install a plurality of capturing units on a detecting unit. In this case, because the detection sensitivity decreases when too many numbers of capturing units are installed on a detecting unit, it is often preferable to make the number of the capturing units installed on a detecting unit as small as possible, by making the size of the detecting unit smaller, making the density of capturing units smaller, or employing other similar measures.

When analytes are captured directly by a detecting unit without an intervening capturing unit, a case may be acceptable in which one detecting unit can capture a plurality of analytes similarly to the above. However, it is also often preferable to make the number of the analytes that can be captured by one detecting unit as small as possible, by making the size of the detecting unit smaller, or employing other similar measures.

When optical signals are utilized, each of analytes captured by a capturing unit emits an optical signal. Accordingly, it is not necessary to install plural detecting units, and it is sufficient if the quantitative measurement unit can divide these signals into a plurality of parts in the direction of the flow in the flow channel for processing.

FIGS. 4-A to 4-C are schematic views of devices for quantitatively determining an analyte where analytes captured by capturing units emit fluorescence. In FIGS. 4-A to 4-C, capturing units that have captured analytes and capturing units that have not captured an analyte are shown. In this case, there are a plurality of capturing units both in the direction of the flow and along the width of the flow channel in one detecting unit. In such a case, the quantitative measurement unit can also divide the signals obtained by the scanning in the direction of the flow in the flow channel, into plural signals in the direction along the width of the flow channel for processing. When there happen to be a case when the numbers of capturing units that have captured analytes in the direction of the flow in the flow channel, are different in the direction along the width of the flow channel, as shown in FIG. 4-C, it is reasonable to use the average value for the quantitative determination, for example.

It is not always necessary for the quantitative measurement unit to divide optical signals for processing according to each analyte, each capturing unit, or each detecting unit. For example, it may be possible to put some analytes, capturing units, and/or detecting units together into a group in the direction of the flow to be subjected to the processing. For example, signals in a certain wavelength range may be grouped for the processing.

It is not always necessary to install a capturing unit if a detecting unit can directly capture an analyte. A case where an analyte is physically or electrically adsobed onto a detecting unit is such a case. However, since such adsorption is generally weak, it is preferable to install a capturing unit that can capture an analyte on the detecting unit. When a plurality of capturing units are used for specifically capturing different analytes, different types of plural analytes can be quantitatively determined at the same time. Accordingly, it is preferable.

It is preferable that the length of the detecting unit or detecting units in the direction of the flow is not less than twice the width of the flow channel. If there is one detecting unit in the direction of the flow, the length of the detecting unit in the direction of the flow is its length, and if there are plural detecting units, the length is the total length. By this, it is easier to capture analytes with a plurality of capturing units or detecting units in the direction of the flow, thus increasing the detection sensitivity.

When the width of the flow channel is larger than the width of one detecting unit, a plurality of detecting units may be installed in the direction along the width of the flow channel. Since the flow channel according to the present invention is as tiny as is seen from the fact that the width is in a range of from 100 μm to 5 mm and the height is in a range of from 1 μm to 1 mm, for example, and the flow rate is generally as small as not more than 10 cm/second, which is in the region of laminar flow, it is not always necessary to install a plurality of detecting units in the direction along the width of the flow channel. However, it is preferable to realize quantitative determination with a higher precision. For example, by subjecting signals obtained by scanning in the longitudinal direction of the flow channel, to averaging in the direction along the width, the same number of data can be obtained through one measurement as those obtained by repeating plural times of measurement with a device for quantitatively determining an analyte that has only one detecting unit in the direction along the width of the flow channel.

While the above explanation is made on cases where analytes are bound to capturing units sequentially from the upstream side to the downstream side of the flow, it is not an essential requirement. Depending on the capturing units and analytes for use, there may be cases wherein the ease and velocity of bonding are not sufficient for the flow rate of the analytes, and therefore, the analytes may not be captured sequentially from the capturing unit in the upstream side to the capturing unit in the downstream side of the flow. In such a case, if the number or the length of detecting units installed as are divided into plural parts in the direction of the flow in the flow channel is large enough, precise determination is possible as long as all the analytes are bound to the capturing units, though they may not be bound to the capturing units sequentially from the upstream side to the downstream side.

In addition, it is also effective to make the thickness of the flow channel at the detecting unit sufficiently thin compared with the effective height of analytes, and/or make the flow rate smaller sequentially by making the thickness of the flow channel thicker as the flow goes down, thus securing the time for analytes that become smaller in number to be bound to capturing units, while the number of detecting units arrayed in series in the direction of the flow of the flow channel is not increased, or the number is increased.

It was found preferable that the thickness of the flow channel is made to be not more than 100 times the effective height of a captured analyte, in order to fully capture the analyte. The effective height of an analyte is the height from the surface of the detecting unit to the highest part of the analyte. The height of the capturing unit is included in the definition, as shown in FIG. 5. FIG. 5 is a schematic partial cross-sectional view of a device for quantitatively determining an analyte, for explaining the height 51 of an analyte 19, taking into consideration the height of a capturing unit 14. The "thickness of the flow channel" 52 in this case is the height from the surface of the detecting unit 53 to the ceiling part of the flow channel 54. If the height of the surface of the detecting unit is located higher than the bottom surface 55 of the flow channel, it is preferable that the detecting unit is installed to the full width of the flow channel, or the sections of the flow channel that are adjacent to the sides of the detecting unit (in the direction along the width of the flow channel) and on which the detecting unit is not located, have a raised bottom surface that is as high as the surface of the detecting unit or higher.

The term "effective" refers to the average value of height when an analyte is actually captured by a detecting unit (numeral 51 in FIG. 5). When the analyte and the capturing unit are molecules, the shapes are taken into consideration. When the analyte and the capturing unit are molecules, it is generally difficult to know the effective height. In such a case, the effective height of an analyte may be determined by employing, as the effective length of the molecule, a value that is 50–80% of the largest length which is obtained when the molecule is stretched.

Furthermore, it is preferable that the thickness of flow channel at the detecting unit is made thicker as the flow goes downstream. There may be a case in which depending on capturing units and analytes for use, the ease and velocity of bonding are not sufficient for the flow rate, and therefore, analytes cannot be bound to the capturing units sequentially from the upstream side to the downstream side of the flow, in a thick flow channel, with the result that the quantitative determination is hindered. The above-described flow channel is particularly useful in such a case.

Furthermore, in a case where analytes are molecules which are wholly or partly charged such as DNA and protein molecules, it is preferable that the detecting unit is an electrode, and an electric potential can be applied to the electrode to electrically attract the charged analytes to the electrode. In this way, binding of the analytes to the capturing unit can be accelerated by applying the electric potential to the electrode, so as to shorten the detection time and improve the detection sensitivity.

Furthermore, it is preferable to be able to change the electric potential to electrically attract the charged analytes to the electrode according to the location of the electrode in the direction of the flow in the flow channel. In this way, for example, it is possible to increase the attracting effect by the electric potential as the flow goes downstream and prevent the sensitivity from being reduced, by changing the electric potential according to the location of the electrode, since the concentration of the analytes in the medium becomes smaller as the flow goes downstream, reducing the analyte capturing efficiency.

In this way, it is possible to quantitatively determine an analyte or analytes with a high sensitivity and a high dynamic range. When it is seen from the viewpoint of a method for quantitatively determining an analyte, it can be considered important to optimize the number of analytes to be captured by the analyte detecting unit, in the direction of the flow in the flow channel. Hereupon, the term "to optimize" refers to selecting conditions for the quantitative determination so that the sensitivity and dynamic range in the quantitative determination of analytes are in a proper range corresponding to the actual purposes of the quantitative determination. Specifically, it is preferable to do the optimization, by changing at least one factor selected from the group consisting of the supply rate of analytes, the length of the detecting unit in the direction of the flow in the flow channel, the number of detecting units in the direction along the width of the flow channel, and the thickness of the flow channel.

Of these, regarding the supply rate of analytes, if the fluctuation of the flow rate is small, and it is easily changed, it is easy to optimize the quantitative determination by changing the flow rate. As a means of transportation for this purpose, micropumps may be utilized. Any means may be utilized such as electrophoretic flow and electroosmotic flow by applying en external electric field, as long as it can transport the medium containing analytes to the detecting unit.

By the device for quantitatively determining an analyte according to the present invention, it is possible to quantitatively determine an analyte in a wide range without lowering the detection sensitivity, greatly improving the capacity of quantitative determination of an analyte. Accordingly, it can be effectively used as part of a MEMS or μTAS.

Any known technology may be utilized for manufacturing a device for quantitatively determining an analyte according to the present invention. The following are some examples.

First, grooves for the flow channel are formed on a substrate. Any material such as glasses, plastics, semiconducting materials, etc. may be used for the substrate, as long as it does not contradict the gist of the present invention. The grooves for the flow channel may be formed by any technology including mechanical processing and etching technologies belonging to the semiconductor processing technologies. It is preferable to cover the surface of the substrate to prevent the solution containing analytes from evaporating or scattering. Needless to say, the cover should be made of a material that is transparent in the wavelength for use in the observation, when it is necessary to optically observe the flow channel.

A detecting unit for detecting an analyte to which a capturing unit is attached is installed on a part of the flow channel. Any material may be used for the detecting unit according to the present invention, as long as it does not contradict the gist of the present invention, and there is no limitation to the shape.

As an analyte according to the present invention, any material may be used as long as it can be quantitatively determined by the device for quantitatively determining an analyte according to the present invention. As an analyte, preferable is a material selected from the group consisting of proteins, DNAs, RNAs, antibodies, natural or artificial single-stranded nucleotides, natural or artificial double-stranded nucleotides, aptamers, products obtained by limited decomposition of antibodies with a protease, organic compounds having affinity to proteins, biomacromolecules having affinity to proteins, complex materials thereof, ionic polymers charged positively or negatively, and arbitrary combinations thereof. Examples of the above-described complex materials according to the present invention may include combined materials from DNAs and negatively-charged polymers, and combined materials from the above-described materials and other materials.

Any type of binding can be utilized for the capturing of an analyte as long as it does not contradict the gist of the present invention, including biological binding, electrostatic binding, physical adsorption, chemical adsorption, etc., as well as chemical bonding such as covalent bonding and coordinate bonding.

For example, glasses, ceramics, plastics, metals, etc. can be used for a detecting unit, to install a capturing unit for capturing an analyte on the surface. The detecting unit may be single-layered or multilayered. It may have a structure other than that of a layer or layers.

Any material can be arbitrarily chosen for the detecting unit depending on the purpose, but Au is particularly preferable. When it is used for an electrode, it is easy to take out electric signals, and to provide electric potential to facilitate capturing of analytes. It is also often easy to fix capturing units on a detecting unit.

Figure 6:
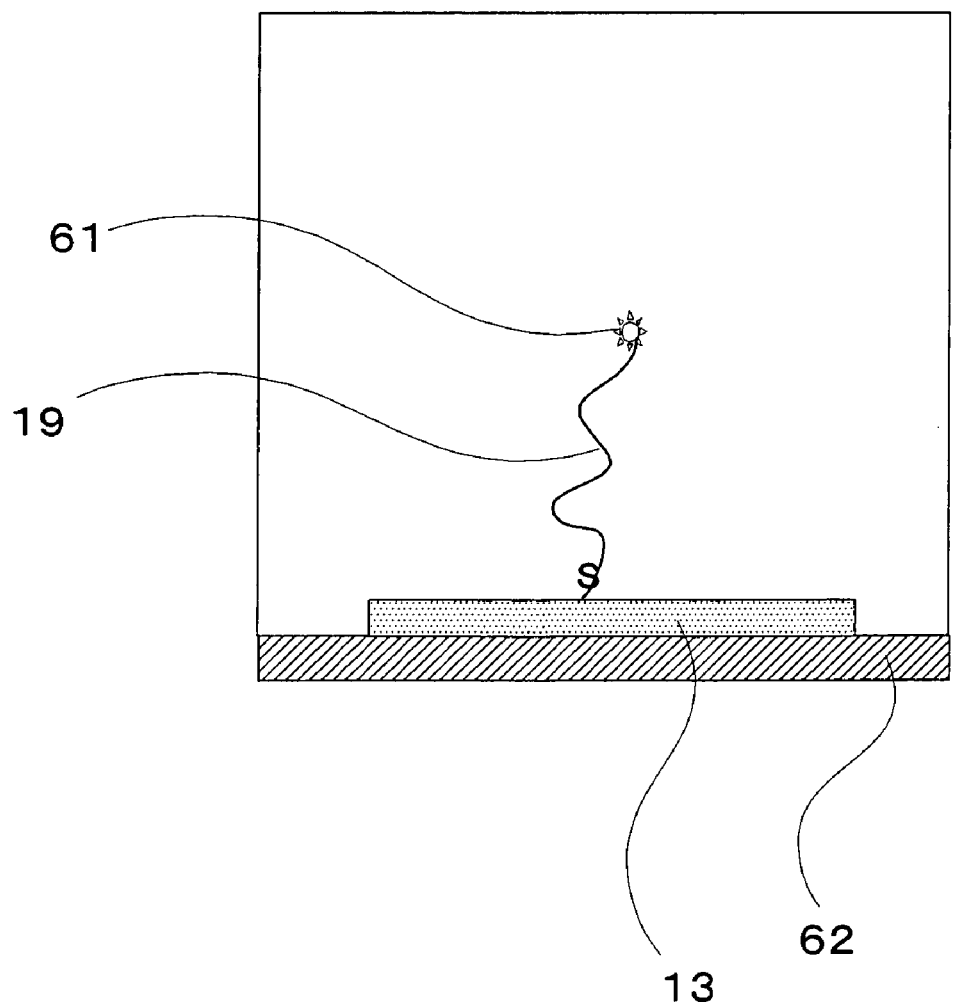
FIG. 6 is a schematic view explaining a device for quantitatively determining an analyte for which no capturing unit is installed.

When the detecting unit can capture an analyte without specifically forming a capturing unit, it is not necessary to install a capturing unit on the surface of the detecting unit. Taking a case in which an analyte comprises a nucleotide, and can be bound with a Au layer directly via its thiol group for example, there is a device for quantitatively determining an analyte, wherein an analyte 19 having a fluorescent signaling unit 61 is bound to a Au electrode (detecting unit 13) installed on a sapphire substrate 62 as shown in FIG. 6, by reacting the nucleotide with the polished Au electrode at room temperature for 24 hours. "S" which is located in the lower portion of the single-stranded oligonucleotide structure represents that the analyte 19 is directly bound with the Au electrode 13 via a thiol group.

Any material may be used as the capturing unit, as long as it does not contradict the gist of the present invention. It is preferable that the material has a property to specifically bind to the above-described analyte. For example, if the analyte is a DNA, it is preferable that the capturing unit has a function to specifically bind to the DNA, and if the analyte is a protein, it is preferable that the capturing unit has a function to specifically bind to the protein.

Preferably, such a capturing unit comprises at least one material selected from the group consisting of proteins, DNAs, RNAs, antibodies, natural or artificial single-stranded nucleotides, natural or artificial double-stranded nucleotides, aptamers, products obtained by limited decomposition of antibodies with a protease, organic compounds having affinity to proteins, biomacromolecules having affinity to proteins, complex materials thereof, ionic polymers charged positively or negatively, and arbitrary combinations thereof. Examples of the above-described complex materials in the present invention may include combined materials from DNAs and negatively-charged polymers, and combined materials from the above-described materials and other materials.

Hereupon, the "nucleotide" according to the present invention is any one selected from the group consisting of mononucleotide, oligonucleotides and polynucleotides, or a mixture thereof. Such materials are often negatively charged. Single-stranded nucleotides and double-stranded nucleotides can be used. They can be specifically bound with analytes through hybridization. Proteins, DNAs and nucleotides can be used as a mixture. The biomacromolecules include those derived from living organisms, those processed from materials derived from living organisms, and synthesized molecules.

Hereupon, the above-described "products" are those obtained by limited decomposition of antibodies with a protease, and can comprise anything, as long as they conform to the gist of the present invention, including Fab fragments or (Fab)₂ fragments of antibodies, fragments derived from Fab fragments or (Fab)₂ fragments of antibodies, derivatives thereof, etc.

As an antibody, monoclonal immunoglobulin IgG antibodies can be used, for example. Fab fragments or (Fab)₂ fragments of IgG antibodies can be used as fragments derived from IgG antibodies, for example. Furthermore, fragments derived from those Fab fragments or (Fab)₂ fragments can be used. Examples of applicable organic compounds having affinity to proteins are enzyme substrate analogs such as nicotinamide adenine dinucleotide (NAD), enzyme activity inhibitors, neurotransmission inhibitors (antagonist), etc. Examples of biomacromolecules having affinity to proteins are proteins that can act as a substrate or a catalyst for proteins, element proteins constituting molecular composites, etc.

It is sufficient if the total number of capturing units to be attached to is sufficiently larger than the number of expected analytes. However, from the viewpoint of detection sensitivity, it is preferably from twice to ten times as large as that of analytes that is expected. When there are plural kinds of analytes as the objects for the quantitative determination, the number of the capturing units should be determined in reference to the number of each kind of analyte.

A device for quantitatively determining an analyte according to the present invention manufactured according to the way of this example, is suitable for determining a tiny amount of minute analytes, and is suitably utilized for the above-described MEMS and μTAS, for example. Regarding the application, it is suitable for biochips, DNA chips, etc, for example.

A method for quantitatively determining an analyte according to the present invention comprises: using a device for quantitatively determining an analyte having the above-described functions, or, regarding a different device, using a flow channel, a detecting unit for capturing and detecting the analyte, and a quantitative measurement unit for quantitatively determining the analyte; and dividing a signal generated when the detecting unit has detected the analyte, into a plurality of parts in the direction of the flow in the flow channel at the quantitative measurement unit for processing. By this method, the quantitative determination of an analyte can be performed in a wide range without lowering the detection sensitivity, and the performance in quantitative determination of an analyte can be conspicuously improved, in the same way as has been explained about the device for quantitatively determining an analyte according to the present invention.

In this case, variations such as using a plurality of devices in series or in parallel, and installing accessories, may be applied. In such a case, there would be an increasing number of defects such as complicated equipment and more time consumed for the measurement, compared with a case in which a device for quantitatively determining an analyte according to the present invention, is used. Nevertheless, it may be possible to accomplish effects similar to those achieved when the device for quantitatively determining an analyte according to the present invention, is used.

Regarding this embodiment of the present invention, preferable are that the detecting unit has a capturing unit for capturing the analyte; that a plurality of detecting units are disposed in the direction of the flow in the flow channel; that the quantitative measurement unit quantitatively determines the analyte, using an optical signal or electric signal; and that a plurality of capturing units for specifically capturing different analytes, are disposed on the detecting unit.

In the quantitative determination, it is possible to improve the performance in the quantitative determination by optimizing the number of analytes captured by the detecting unit, in the direction of the flow in the flow channel, as has been already explained regarding the device for quantitatively determining an analyte according to the present invention. Specifically, it is possible to do the optimization, by changing at least one factor selected from the group consisting of the supply rate of analytes, the length of a detecting unit in the direction of the flow, the number of detecting units in the direction along the width of the flow channel, and the thickness of the flow channel.

Furthermore, it is preferable that the detecting unit is an electrode, and an electric potential for electrically attracting a charged analyte to the electrode is applied to the electrode, in order to rapidly capture the analyte by the capturing unit. In such a case, the electric potential may be determined appropriately, in consideration of the time required for the quantitative determination and the precision of the quantitative determination.

It is useful to change the electric potential for electrically attracting a charged analyte to the electrode according to the location of the electrode in the direction of the flow. As the concentration of analyte in the medium is lowered as the flow goes downstream, the capturing efficiency of analyte is lowered. Accordingly, it is useful to change the electric potential according to the location of the electrode, and increase the attracting effect of the electric potential as the flow goes downstream, so that the sensitivity is prevented from being lowered.

It is to be noted that the method for quantitatively determining an analyte according to the present invention is particularly useful when the analyte is a DNA, and the capturing unit has a function to be specifically bound to a DNA, and when the analyte is a protein, and the capturing unit has a function to be specifically bound to a protein.

Next, the explanation on the second aspect of the present invention will be made. When required molecules are attached to the surface of a solid, it is a common method to immerse the solid into a solution containing the molecules. At this moment, electrostatic repulsion between molecules will come about, when molecules that are charged (acquiring electric charge) in a solution, or those that are bound with materials having electric charge are used as the attached molecules. Because of this, other molecules are prevented from coming close to the molecules attached to the surface of a solid by the electrostatic repulsion.

It is to be noted here, that molecules that are charged, molecules that are bound with materials having an electric charge, or the like are generally called simply "molecules that are charged" or "charged molecules" in the second aspect of the present invention. The detail will be explained later.

When an aqueous solution containing an electrolyte is used as the solvent, the molecules are surrounded with ions (counter ions) having an electric charge that is opposite to that of the molecules with a certain distance therebetween that is determined by the probability of occurrence, and accordingly, the electric charges are neutralized by the ions. This effect of compensating the charges between molecules is called the screening effect, and the layer of these counter ions is called the diffused electric double layer.

The thickness of the diffused electric double layer is dependent on the salt concentration of the electrolyte (ion concentration of the electrolyte), and the higher the salt concentration is, the thinner the layer is. The thickness of the layer is widely known as the Debye length ($L_{Debye}$). It can be expressed by the following equation in the case of a 1:1 type electrolyte (an electrolyte composed of a pair of a monovalent cation and a monovalent anion).

$$L_{Debye}=(2{,}000 N_A c z^2 e^2/(\epsilon_r \epsilon_0 kT))^{-1/2} \; (m) \qquad (1)$$

Hereupon, $N_A$ is the Avogadro's number, c is the ion concentration of the electrolyte (mol/L), z is the valence of the ion, e is a unit charge, $\epsilon_r$ is the relative dielectric constant of a medium, $\epsilon_0$ is the dielectric constant of vacuum, k is the Boltzmann constant, and T is the absolute temperature.

Figure 7:
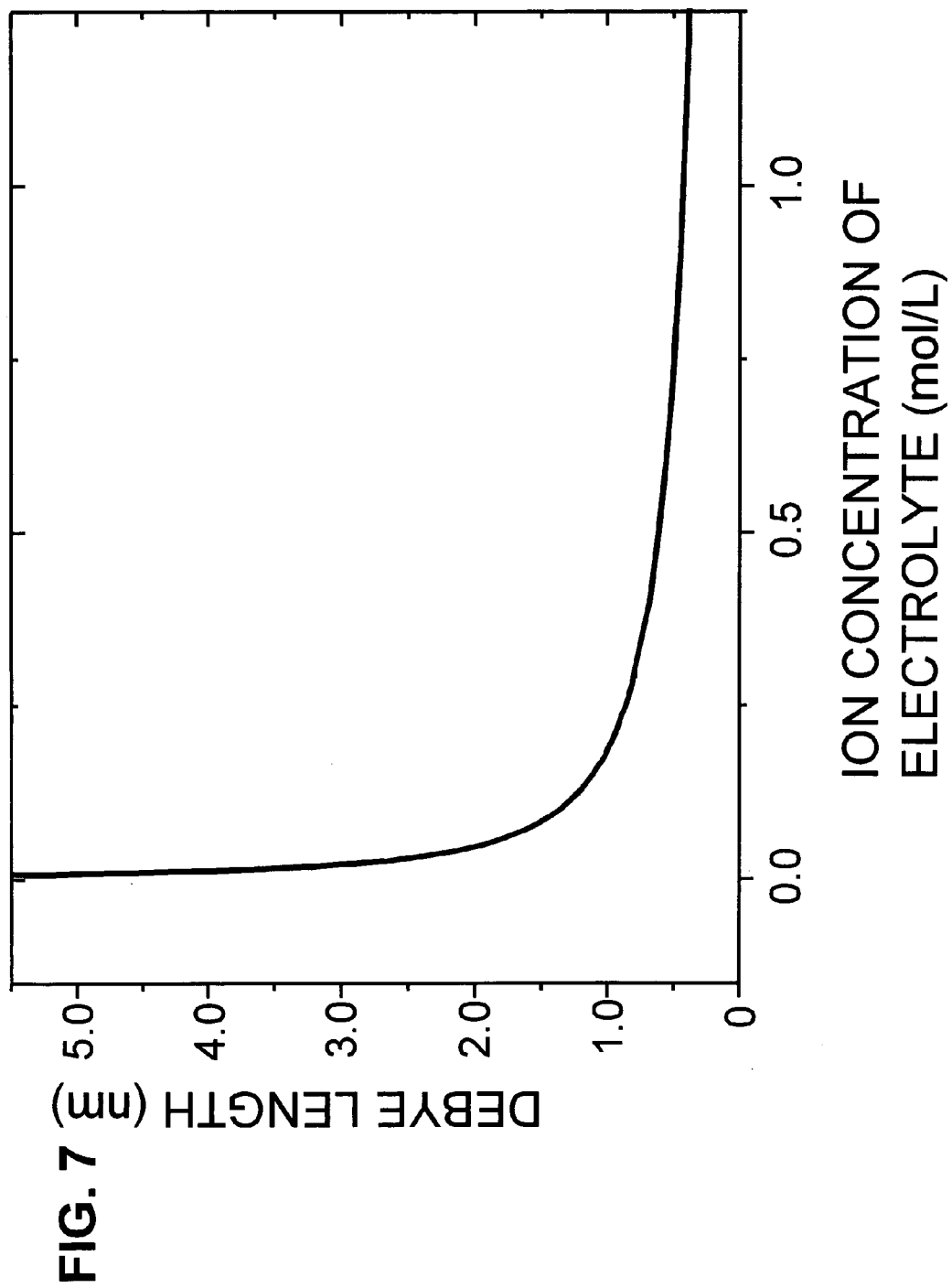
FIG. 7 is a graph showing the dependency of a Debye length on the ion concentration of the electrolyte, when a 1:1 type analyte is used.

From this equation, it is possible to easily estimate the change of $L_{Debye}$ when the ion concentration is changed. FIG. 7 shows the change of $L_{Debye}$ when the ion concentration of a 1:1 type electrolyte such as NaCl is changed. It is understood that $L_{Debye}$ is small in a region where the ion concentration is high, and accordingly the screening effect is large. That is, it is possible to conclude that the electrostatic repulsion between charged molecules can be restrained, and accordingly, a film of charged molecules with a high attaching density can be manufactured, in such a region of ion concentration. Furthermore, more precise control of the attaching density is possible, by taking into consideration, the screening effect and the size of charged molecules in the solution.

In this way, it is possible to uniquely calculate $L_{Debye}$, when what electrolyte ion is used, is determined. Furthermore, if the size of a charged molecule in a solution is known, it is possible to estimate, by the calculation, the attaching density of charged molecules that changes according to the ion concentration, taking into consideration the size and $L_{Debye}$.

An example in which the charged spherical molecules that are negatively charged and have a radius of 1 nm, are attached to the surface of a solid, will be explained as follows.

Figure 8:
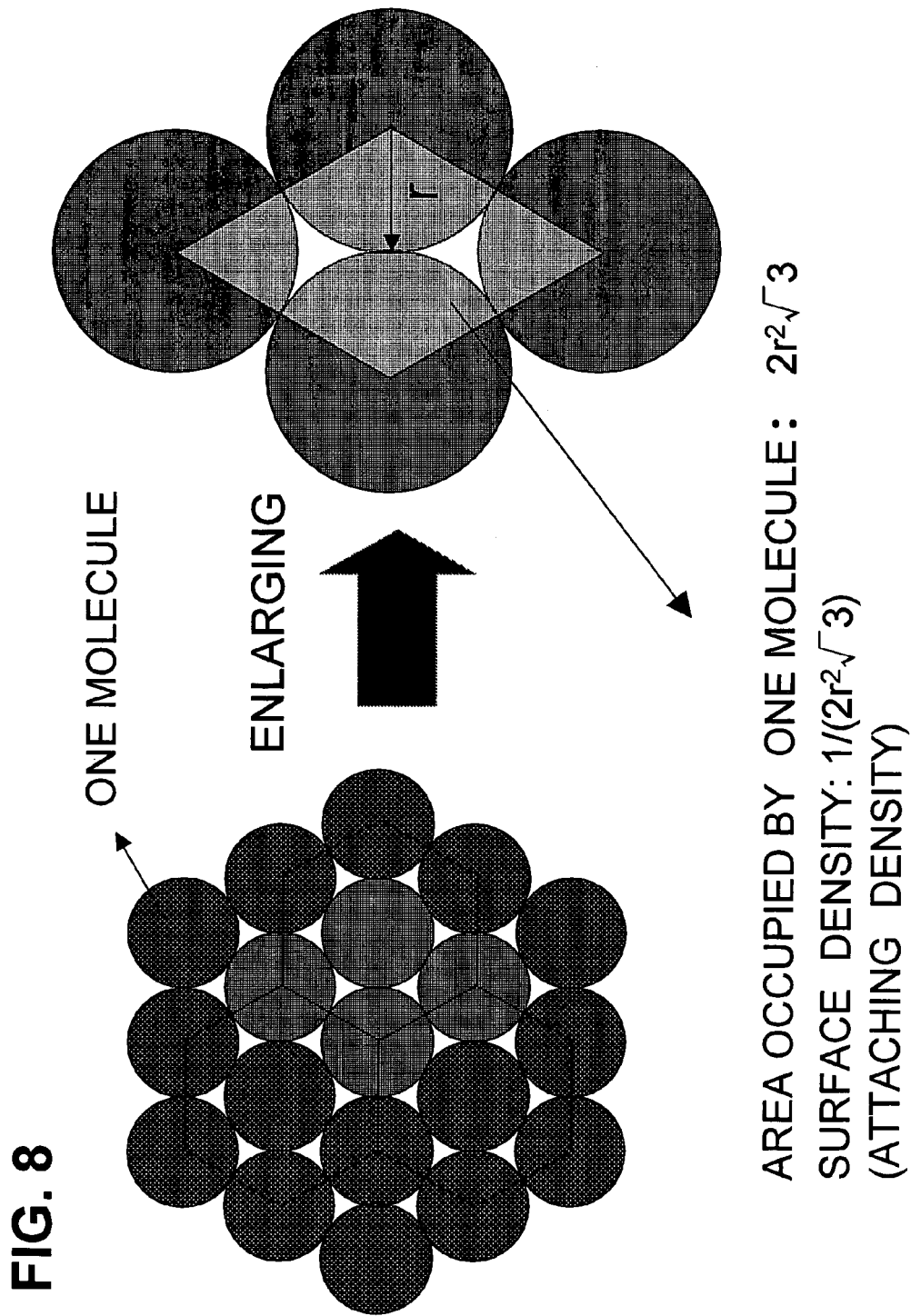
FIG. 8 is a schematic view showing the closest packing structure of molecules attached to a substrate, and the principle to calculate the attaching density.

When a case is provided where there occurs no electrostatic repulsion between charged molecules, and a monomolecular film is adsorbed to a flat surface of a solid, it is possible to consider that a film of hexagonally arranged molecules is formed as a closest packing structure as shown in FIG. 8. In this case, the attaching density (thickest surface density) of molecules can be represented, using the radius r of the molecule, by:

$$\text{Attaching density}=1/(2r^2\sqrt{3})(\text{cm}^{-2}) \qquad (2).$$

When the r is 1 nm for the molecule, a constant attaching density of $2.9\times 10^{13}$ cm$^{-2}$ is obtained.

Figure 9:
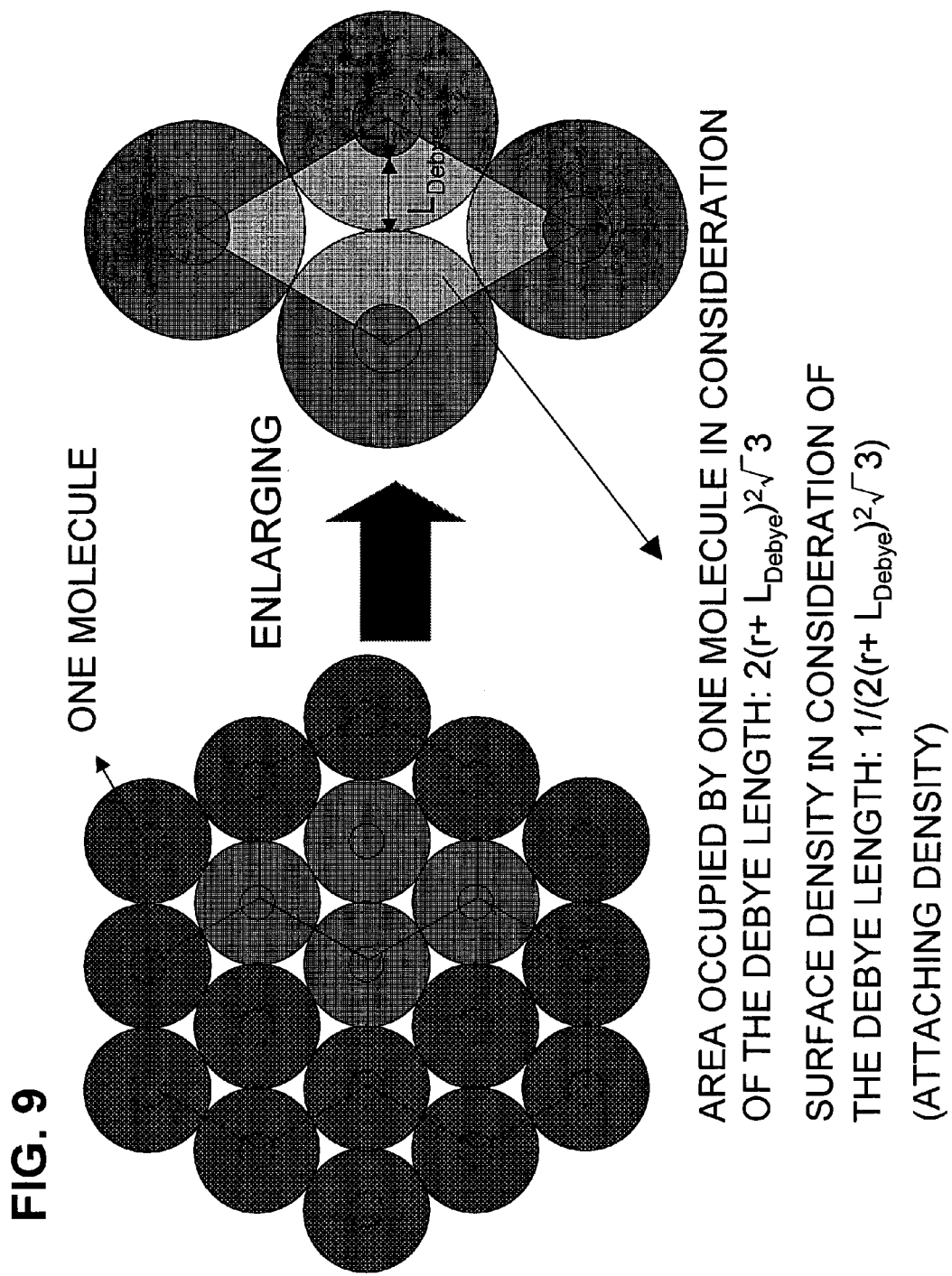
FIG. 9 is a schematic view showing the closest packing structure of molecules attached to a substrate, and the principle to calculate the attaching density, when the Debye length is taken into consideration.

When the static repulsion between charged molecules and $L_{Debye}$ are taken into consideration, the layer of adsorbed molecules has molecules having a separation of $L_{Debye}\times 2$ therebetween as shown in FIG. 9, and the attaching density can be represented by the following equation.

$$\text{Attaching density}=1/(2(r+L_{Debye})^2\sqrt{3})(\text{cm}^{-2}) \qquad (3)$$

Figure 10:
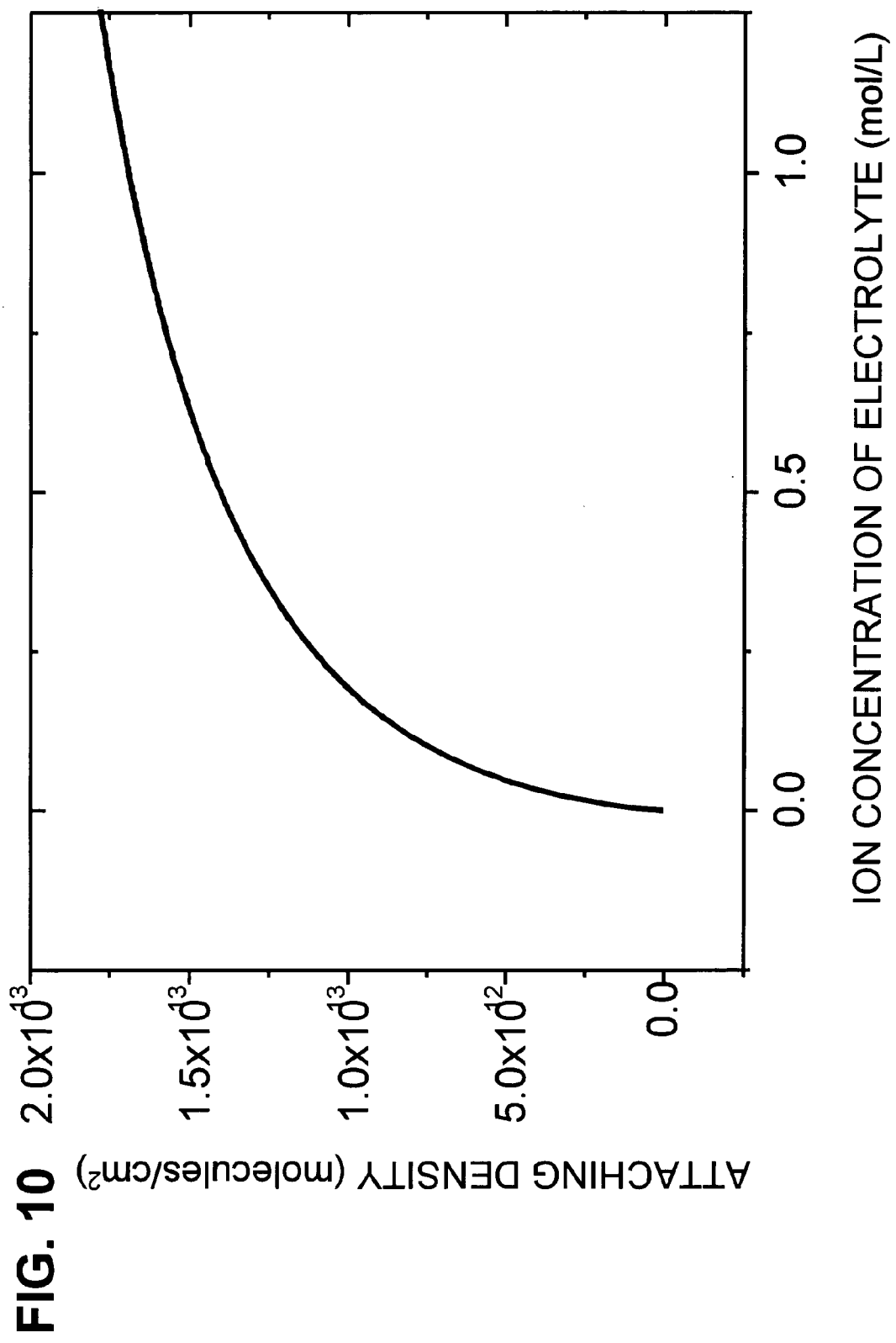
FIG. 10 is a graph showing the dependency of the attaching density of adsorbed molecules on the ion concentration of the electrolyte, when the attaching density is calculated, taking the Debye length into consideration.

Accordingly, for a case where a 1:1 type electrolyte such as NaCl is used, and the molecule has a radius of 1 nm, it is possible to control the attaching density by changing the ion concentration of the electrolyte, as shown in FIG. 10.

The above is about cases when the size of a charged molecule in a solution is known. However, even if the size is unknown, it is possible to estimate the size of the unknown molecule from the experimental data obtained by measuring the attaching density of charged molecules at a specific ion concentration of an electrolyte through experimentation, and accordingly, to estimate the dependency of the attaching density on the ion concentration, taking into consideration, the size and screening effect.

In other words, in the effective size decision method of charged molecules according to the present invention, the effective size of a charged molecule in a solution containing an electrolyte and the charged molecules is estimated by the screening effect by the electrolyte.

Specifically for example, the effective size of a charged molecule can be determined as a radius of a molecule, when the Debye length is determined from the ion concentration of the electrolyte, using equation (1), and the Debye length and the measured attaching density data of charged molecules are applied to equation (3). The attaching density in this case can be obtained by a quantitatively determining method using XPS observing a specific element of the attached molecules, a quantitatively determining method wherein radioactive labels are attached to the attached molecules beforehand, a quantitatively determining method to measure the redox current of a redox marker to neutralize the charge of the charged, attached molecules, etc.

Any material may used as the electrolyte for use in this case, as long as it does not contradict the gist of the present invention. It is preferably a 1:1 type electrolyte such as NaCl or KCl, from the viewpoint of simplifying the effect on the charged molecules. A mixture thereof may be used.

The "charged molecule" according to the second aspect of the present invention includes molecules that simply have a charge as explained earlier, those having acquired a charge as a cluster of molecules having an electric charge or not having an electric charge, and a material having an electric charge, as a result of the molecules being bound with the material, and those acquired a charge as a cluster of molecules having an electric charge and a material not having an electric charge, as a result of binding of the molecules with the material. In the latter two cases, a cluster is the "charged molecule" according to the present invention. In this case, the "binding" may be chemical binding or physical binding. The former is better because the binding stability is higher and is preferable.

The above-described material is preferably selected from the group consisting of proteins, DNAs, RNAs, antibodies, natural or artificial single-stranded nucleotides, natural or artificial double-stranded nucleotides, aptamers, products obtained by limited decomposition of antibodies with a protease, organic compounds having affinity to proteins, biomacromolecules having affinity to proteins, complex materials thereof, ionic polymers charged positively or negatively, and arbitrary combinations thereof. Molecules that can be bound to such a material preferably have a property to be specifically bound to the material.

Therefore, the "charged molecule" according to the present invention preferably comprises a material selected from the group consisting of proteins, DNAs, RNAs, antibodies, natural or artificial single-stranded nucleotides, natural or artificial double-stranded nucleotides, aptamers, products obtained by limited decomposition of antibodies with a protease, organic compounds having affinity to proteins, biomacromolecules having affinity to proteins, complex materials thereof, ionic polymers charged positively or negatively, and arbitrary combinations thereof. The "charged molecule" according to the present invention preferably comprises a thiol group to facilitate attachment to a substrate.

Hereupon, the "nucleotide" according to the present invention is any one selected from the group consisting of mononucleotide, oligonucleotides and polynucleotides, or a mixture thereof. Such materials are often negatively charged. Single-stranded nucleotides and double-stranded nucleotides can be used. They may be hybridized to be part of charged molecules. Proteins, DNAs and nucleotides can be used as a mixture. The biomacromolecules include those derived from living organisms, those processed from materials derived from living organisms, and synthesized molecules.

Hereupon, the above-described "products", the "antibody", organic compounds having affinity to proteins, and biomacromolecules having affinity to proteins, have each the same meaning and may have the same examples as described before.

It is to be noted that the "charged molecule" according to the present invention may acquire a role to make the surface of a substrate either hydrophobic or hydrophilic, by the attaching to the substrate, and a role to provide functions which the original surface of a solid has not had, by the adsorption of special molecules such as DNAs and proteins to the surface. A specific example is formation of a monolayer film having a functionality, by making the surface hydrophobic by covering it with —$CH_3$, making the surface hydrophilic by covering it with $NH^{3+}$ or $COO^-$ to form either a positively charged surface or a negatively charged surface, making the surface adsorb DNAs or proteins, or by doing a similar modification.

In the method for attaching charged molecules onto a substrate according to the present invention, an electrolyte is made present in the solution containing the molecules, and the screening effect by the electrolyte is adjusted in order to attach charged molecules to the substrate. The effective size of a molecule in the solution is also taken into consideration.

For example, because the attaching density, the Debye length and effective size of a molecule are interconnected with each other through equation (3), it is possible to calculate a desired Debye length from the effective size of a molecule to be attached and a desired attaching density, and determine the kind of an electrolyte and its ion concentration to meet the Debye length. Accordingly, it is possible to make molecules attach to a substrate so that the surface of the substrate has the required attaching density.

In this case, if the effective size of a molecule is known, the size may be used. When the effective size of a molecule is unknown, the effective size of a charged molecule in a solution containing an electrolyte and the charged molecules may be estimated from the screening effect by an electrolyte, as described above. As an electrolyte in this case, a 1:1 type electrolyte is preferably used.

When this method is employed, it is possible to obtain a device to attach charged molecules to a substrate in which the density of molecules attached to the substrate can be controlled. Any device may be used for the device as long as it meets the object of the present invention. For example, this device may be installed as a part or accessory of a MEMS that is a precision system in which a plurality of functional parts such as mechanical, optical and hydrodynamic parts are integrated and miniaturized, or a μ-TAS that is a chemical analysis system with micropumps, microvalves, sensors or the like, miniaturized, accumulated, and integrated, both systems being manufactured, using technologies for preparing very small devices, based on semiconductor processing technologies. As a MEMS or μ-TAS, specifically enumerated are an ion sensor such as a pH sensor and gas sensor, and a device for detecting molecules such as a DNA chip and protein chip for use in detecting wholly or partly charged molecules such as DNAs and proteins. It is to be noted that "detection" in the present invention includes determining the presence or absence of charged molecules or molecules that are specifically bound to a material that is bound with the charged molecules, and determining the kind, size and/or amount of charged molecules or the material that is bound with the charged molecules.

Using this device, it is possible to observe the motion of charged molecules in a state in which there is no interactive influence between the charged molecules or to evaluate the interactive influence between charged molecules, by selecting a desired value of the attaching density of charged molecules on a substrate.

As a molecule detecting device for use in detecting charged molecules so as to observe the motion of the charged molecules in a state in which there is no interactive influence between the charged molecules, it is preferable to use the above-described method for attaching molecules to a substrate, and use, as the molecule detecting unit, a substrate whereby the attaching density is controlled so that the distance between adjacent molecules attached to the substrate is not less than twice the effective length of a molecule, preventing the molecules from physically contacting each other.

In addition, as a molecule detecting device for use in detecting charged molecules in order to evaluate the interactive influence between charged molecules, it is preferable to use the above-described method for attaching molecules to a substrate, and use, as the molecule detecting unit, a substrate whereby the attaching density is controlled so that the distance between adjacent molecules attached to the substrate is less than twice the effective length of a molecule, making the molecules physically contact each other.

It is to be noted that the above distance between adjacent molecules can be determined from the attaching density.

In such a device for detecting molecules, any known method may be used as a method for detecting molecules. Examples are a method in which voltage is applied between a substrate and a solution containing an electrolyte, and an electric signal is taken out as the response, a method in which a fluorescent pigment is attached to charged molecules, and the fluorescence is detected, or similar other methods.

Figure 13:
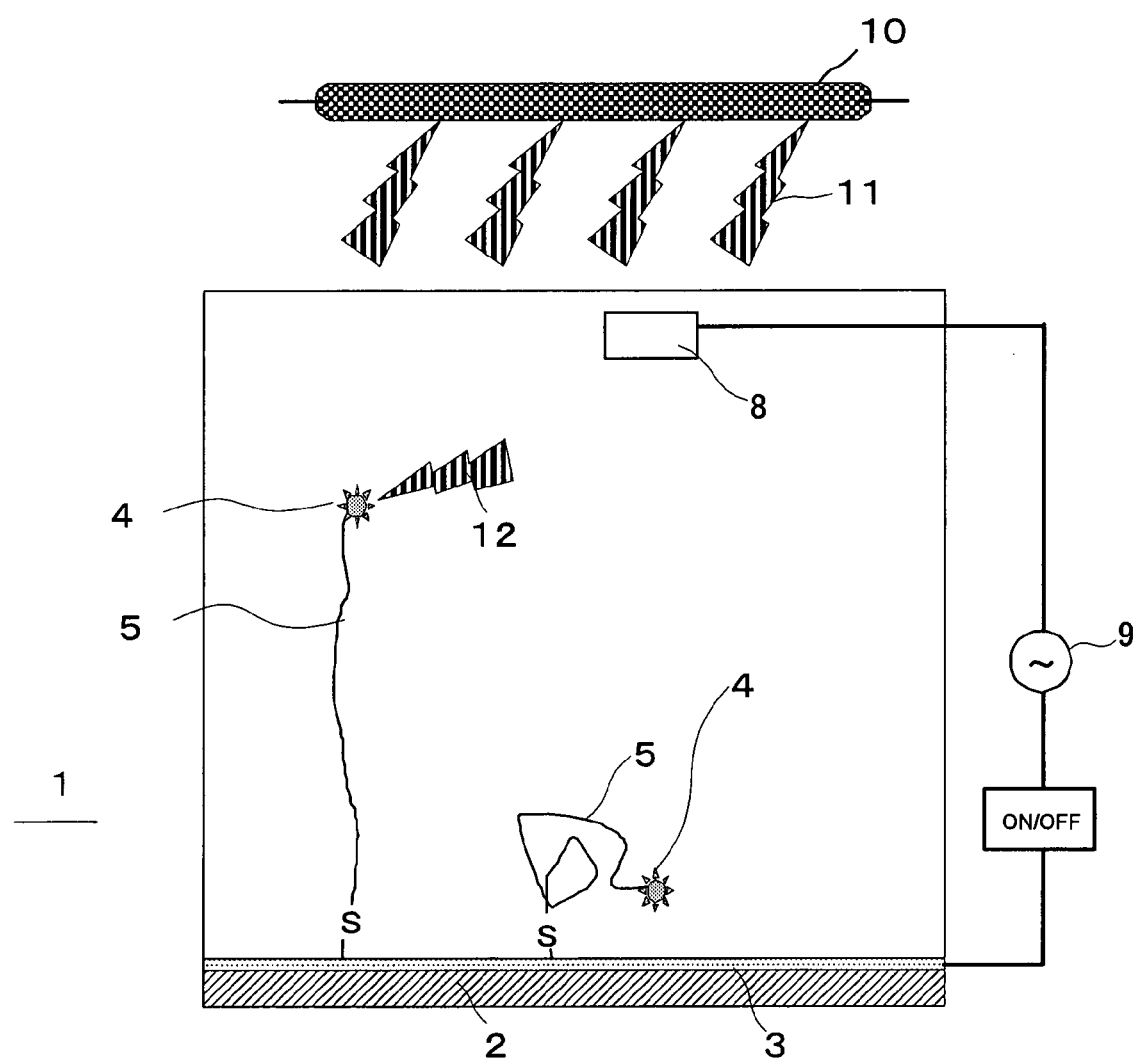
FIG. 13 is a schematic view showing an example of a device for detecting molecules, wherein a fluorescent pigment is attached to charged molecules for the fluorescence to be detected.

FIG. 13 shows an example of a device for detecting molecules, wherein a fluorescent pigment is attached to charged molecules for the fluorescence to be detected. The device 1 for detecting molecules in FIG. 13 shows states of a charged molecule 5 having a fluorescent pigment 4 in an extended state (on the left), and a charged molecule 5 having a fluorescent pigment 4 in a contracted state (on the right), on a Au electrode 3 (corresponding to a substrate according to the present invention) installed on a base 2. The charged molecule 5 in the contracted state can be changed into one in an extended state, by applying a certain potential difference between the Au electrode 3 and a counter electrode 8 with an external electric field applying device 9. By this, the distance between the fluorescent pigment 4 and the Au electrode 3 changes. At this moment, if light 11 is irradiated from a light irradiating device 10, fluorescence 12 is obtained from the charged molecule 5 in the extended state (on the left).

Using the device for detecting molecules according to the present invention, it is possible to control the attaching density of molecules attached to the surface of a solid, and accordingly, it is possible to clarify the structure and/or behavior of molecules attached to the surface of a solid in a solution, and to realize a device using molecules attached to the surface of a solid with high reliability and high sensitivity.

For example, if a DNA or antibody is used for charged molecules attached to the surface of a substrate, and the density is quantitatively controlled, the structure and/or behavior of the targeted DNA or protein in an aqueous solution can be clarified. Also, by optimizing the detection conditions through these pieces of information, devices with high reliability and high sensitivity can be realized. Accordingly, it will be easy to evaluate the presence or absence of a target, and/or to determine the kind, size and/or amount of the target.

In addition, the technology of the present invention is very effective in the field of biosensors such as MEMSs or μTASs, since it is necessary to provide a state in which these molecules are sufficiently apart from each other (that is, a state in which there is no steric hindrance), with a high reproducibility, when the observation of the electric and/or physical properties of each molecule on a functional surface is applied to those biosensors.

Furthermore, when the interactive action between a molecule and the surrounding molecules is necessary in such cases as bonding between attached molecules, exchanging of charges between molecules, optical energy transfer, etc., it is necessary for these molecules to be sufficiently close to each other, in contrast with the above. The technology of the present invention is also very effective in such a field.

Furthermore, the technology of the present invention can greatly contribute to the elucidation of functions of charged molecules with unknown behaviors in an aqueous solution. Accordingly, discovery of new functional materials and functional surfaces may be highly expected.

It is to be noted that for the substrate according to the present invention, any of electroconductive materials such as metals, semiconducting materials such as silicon, and insulating materials such as glasses, ceramics, plastics and sapphire, may be used, according to purposes. As the electroconductive material, an electroconductive substance itself as well as one having an electroconductive layer on the surface of a glass, ceramic, plastic or metal may be used. As the electroconductive substance, any substance may be used, including an elementary metal, alloy, or laminate. Noble metals represented by Au is preferably used as they are chemically stable.

EXAMPLES

The present invention will be explained in detail in reference to the following examples.

Example 1

This example relates to a DNA chip wherein a single-stranded DNA is installed on a detecting unit as a capturing unit, to detect the concentration of a complementary DNA or an analyte in an aqueous solution.

The outline of an exemplary DNA chip of this example and its basic principle of operation will be explained, using FIGS. 4-A to 4-C. First, as shown in FIG. 4-A, a Au thin film is installed as a detecting unit 13 at the bottom of part of a 1-mm wide flow channel in an elongated shape along the flow channel. A single-stranded DNA 42 having an SH group on one end as a capturing unit is attached onto the Au thin film 13 at a surface density of $5 \times 10^{12}$ molecules/cm$^2$ (see Analytical Chemistry, vol. 70, p. 4670–4677, 1998, for example), to make capturing units. A two-dimensional CCD light-receiving unit 41 is installed over the flow channel with the single-stranded DNA attached thereto, for observing fluorescent signals from the capturing units.

Next, as shown in FIG. 4-B, an aqueous solution containing a complementary DNA 43 as an analyte with a fluorescent label 44 is made to flow into the flow channel, to hybridize with the single-stranded DNA 42 to form double strands as shown in FIG. 4-C. Regarding the units that have formed double strands, fluorescence from the fluorescence labels 44 attached to the complementary strands is detected by the light-receiving unit 41.

As the aqueous solution containing an analyte flows into the detecting unit from the upstream side, the formation of the double strands starts at the upstream side of the detecting unit, and advances towards the downstream side until the analyte is consumed. Because the number of capturing units on the detecting unit is determined through the above-described surface density, the number of the complementary DNA or analyte, that is, the concentration can be determined from the length of the capturing units detected through the fluorescent signals.

In this example, the width of the flow channel is 1 mm. Therefore, when the fluorescent signals are observed 5 mm long along the direction of the flow in the flow channel, the area in which the fluorescent signals are observed is 0.05 cm$^2$, and accordingly, the absolute number of the complementary DNA molecules is $5 \times 10^{12}$ molecules/cm$^2 \times 0.05$ cm$^2 = 2.5 \times 10^{11}$ molecules. Accordingly, if the volume of the used solution containing the complementary DNAs is, for example, 100 μL, the original concentration of the analyte or the complementary DNA, can be determined as $2.5 \times 10^{11}$ molecules/(0.1 cm$^3$)=$2.5 \times 10^{12}$/cm$^3$ molecules.

Example 2

This example relates to determining the effective radius of a single-stranded oligonucleotide in an aqueous solution, and further, to controlling the attaching density of oligonucleotide attached to a substrate.

Synthesized was a single-stranded 24-mer oligonucleotide to which a thiol group having a $C_6H_{12}$ alkyl chain (—$C_6H_{12}$—SH) at the 3' terminal was introduced, and the thiol group was reacted with a polished Au electrode at room temperature for 30 minutes, to bind the single-stranded oligonucleotide to the electrode. The thiol group may be introduced to an intermediate section of a single strand or at the 5' terminal. The aqueous solution used for the reaction contained 10 mM of a Tris buffer (2-amino-2-hydroxymethylpropane-1,3-diol), and adjusted to have a pH of 7.4.

NaCl was used as an electrolyte. The screening effect of a negatively charged oligonucleotide was controlled, by changing the ion concentration of the electrolyte (salt concentration). Since the effective size of the oligonucleotide in the aqueous solution was unknown, while the structure was known, the attaching density of the oligonucleotide attached to the surface of the Au electrode was measured, by reacting the thiol group of the single-stranded oligonucleotide with the Au electrode beforehand, under the salt concentration conditions of 3 mM, 500 mM, and 1,000 mM.

Figure 11:
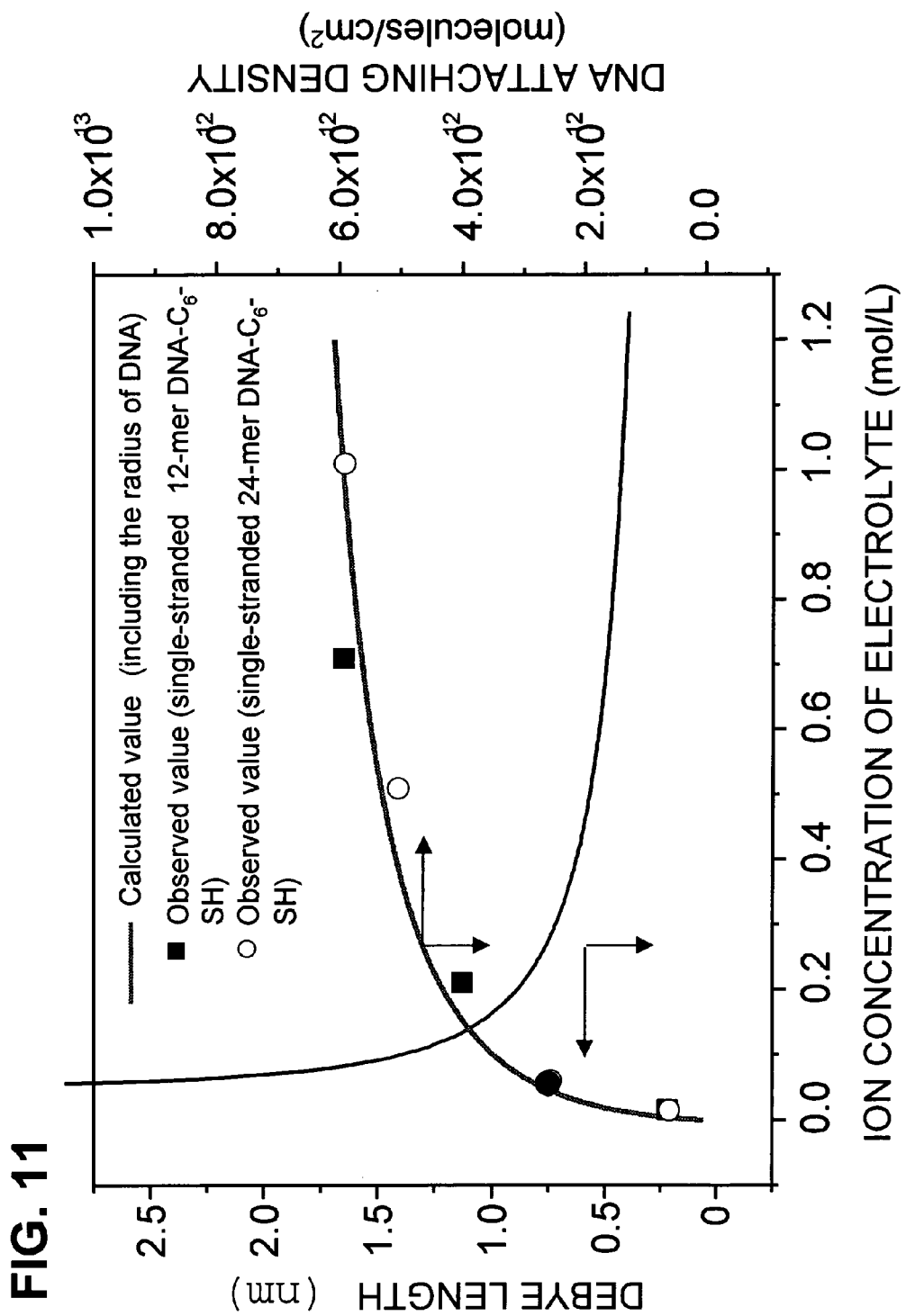
FIG. 11 is a graph showing the relationship between the attaching density of single-stranded oligonucleotide molecules and the ion concentration of the electrolyte, and the relationship between the Debye length and the ion concentration of the electrolyte.

FIG. 11 is a graph showing the relationship between the attaching density of single-stranded oligonucleotide molecules and the ion concentration of the electrolyte, and the relationship between the Debye length and the ion concentration of the electrolyte. The ○ (outlined circle) marks in FIG. 11 are attaching density data determined through experimentation. As a result of calculation by fitting the experimental results onto the calculated curves obtained from equations (1) and (3), the effective size of the 24-mer oligonucleotide in the aqueous solution was decided to be 1.9 nm in radius.

To obtain an electrode surface that is controlled to have a desired attaching density of $3 \times 10^{12}$ molecules/cm$^2$ from this calculated curve, it is understood that the salt concentration must be controlled to be 50 mM, based on the curve obtained by the calculation. The ● (solid circle) mark in the figure is an experimental data when the oligonucleotide was attached at the salt concentration of 50 mM. From the calculation, it is possible to easily determine the salt concentration condition to obtain a desired attaching density.

In addition, ■ (solid square) marks show the result of attaching experimentation when a single-stranded, 12-mer oligonucleotide having a similar thiol group was used. As a result of calculation by fitting the experimental results onto the calculated curves obtained from equations (1) and (3), it was found that the molecule also had an effective size similar to that of the 24-mer in an aqueous solution. The single-stranded, 12-mer oligonucleotide and the single-stranded, 24-mer oligonucleotide are each molecule in the shape of a strand. Accordinly, from the fact that the Debye length's are not different from each other, it is considered that in a case where a strand-type molecule one end of which is modified with a thiol group is chemically adsorbed onto a substrate, the length of the molecule does not influence the effective size and Debye length.

In this way, by utilizing the present invention, it is possible not only to control the attaching density of charged molecules such as oligonucleotide molecules, but also to estimate the effective size of an unknown molecule in aqueous solutions, and to collect information on the state of the attaching.

Example 3

Figure 12:
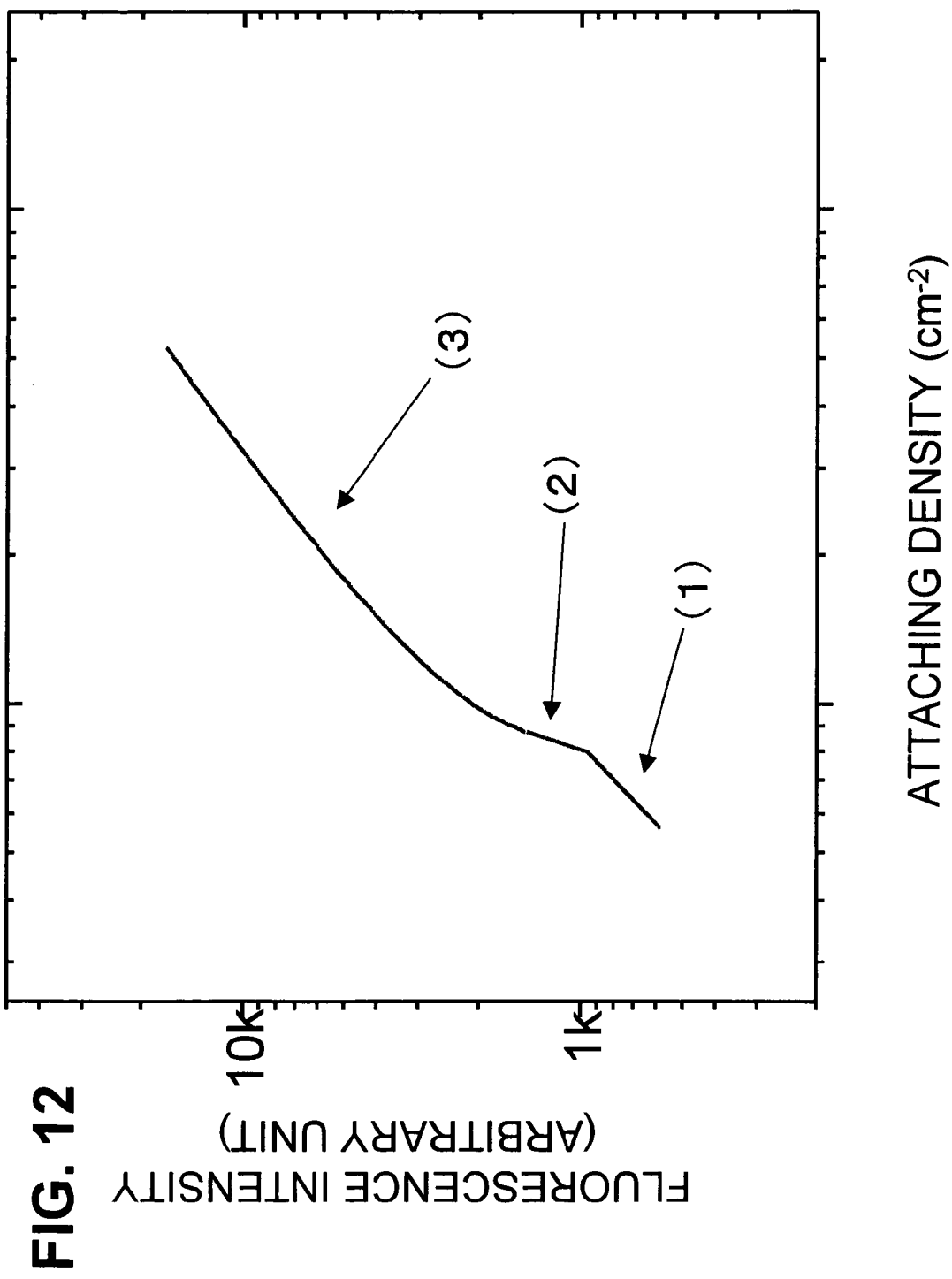
FIG. 12 is a graph showing the relationship between the fluorescence intensity and the attaching density.

As a related example, the above-described method was employed, and single-stranded, 12-mer oligonucleotide molecules having a fluorescent pigment at an end, and a thiol group at the other end were attached to a Au electrode. The result of monitoring the fluorescence from the pigment with varying the density of the attached molecules is shown in FIG. 12. This fluorescent pigment decreases or extinguishes the light by the quenching effect when it comes close to or contacts with the Au substrate, and emits or increases the light when it goes away from the substrate.

From FIG. 12, it is evident that by varying the attaching density, there appear three regions observed: (1) a low density region where adjacent oligonucleotide molecules do not interfere with each other, and the fluorescence intensity is dependent only on the increase in the attaching density; (2) a intermediate density region where steric hindrance between adjacent oligonucleotide molecules occurs, forcing the oligonucleotide molecules to uprise, with the result that the quenching effect on the Au substrate is made smaller, and therefore, the fluorescence intensity is greatly increased owing to the increase in the attaching density and the decrease in the quenching effect; and (3) a high density region where almost all oligonucleotide molecules are uprising, the quenching effect does not change, and the fluorescence intensity is again dependent only on the increase in the attaching density.

From these result, it is possible, by utilizing the present invention, to provide a device in which the attaching density is controlled in region (1), when the device is used for applications where a free motion of oligonucleotide molecules is permitted, without being hindered by surrounding nucleotide molecules. It is also possible to provide a device in which the attaching density is controlled in region (2) or (3), when the interactive actions with surrounding molecules are necessary in such a case as one in which attached molecules are bound together, one in which electric charges are exchanged or optical energies are transferred between molecules, or the like.

What is claimed is:

1. A method for determining an effective size of a molecule having an electric charge the method, comprising the steps of:

measuring the attaching density of a film of said molecules, hexagonally arranged; and calculating said effective size of said molecule in a solution containing an electrolyte, said effective size being the value of r in the following equation:

Attaching density=$1/(2(r+L_{Debye})^2\sqrt{3})(cm^{-2})$, wherein $L_{Debye}$ is the calculated Debye length in said solution.

2. A method for determining an effective size of a molecule having an electric charge according to claim 1, wherein said electrolyte is composed of a monovalent cation and a monovalent anion.

3. A method for determining an effective size of a molecule having an electric charge according to claim 2, wherein said electrolyte that is composed of a monovalent cation and a monovalent anion is NaCl, KCl or a mixture thereof.

4. A method for determining an effective size of a molecule having an electric charge according to claim 1, wherein said molecule comprises a material selected from the group consisting of proteins, DNAs, RNAs, antibodies, natural or artificial single-stranded nucleotides, natural or artificial double-stranded nucleotides, aptamers, products obtained by limited decomposition of antibodies with a protease, organic compounds having affinity to proteins, biomacromolecules having affinity to proteins, complex materials thereof, ionic polymers charged positively or negatively, and arbitrary combinations thereof.

5. A method for determining an effective size of a molecule having an electric charge according to claim 1, wherein said molecule comprises a thiol group.

6. A method for determining an effective size of a molecule having an electric charge according to claim 1, wherein said molecule comprises a fluorescent pigment.

* * * * *